United States Patent [19]

Pavlidis

[11] Patent Number: 4,889,422

[45] Date of Patent: * Dec. 26, 1989

[54] METHOD AND MEANS FOR DETECTING DYSLEXIA

[76] Inventor: George Pavlidis, Park La., Apt. 9E, New Brunswick, N.J. 08901

[*] Notice: The portion of the term of this patent subsequent to Jun. 13, 2006 has been disclaimed.

[21] Appl. No.: 823,464

[22] Filed: Jan. 28, 1986

[51] Int. Cl.⁴ .............................................. A61B 3/14
[52] U.S. Cl. .................................... 351/210; 128/745
[58] Field of Search ................. 351/210, 211; 128/745

[56] References Cited

U.S. PATENT DOCUMENTS

| | | |
|---|---|---|
| 3,473,868 | 10/1969 | Young et al. |
| 3,583,794 | 6/1971 | Newman |
| 3,679,295 | 7/1972 | Newman |
| 3,689,135 | 1/1971 | Young et al. |
| 3,842,822 | 10/1974 | Levinson et al. |
| 3,864,030 | 2/1975 | Cornsweet |
| 3,952,728 | 4/1976 | Levinson et al. |
| 3,970,990 | 7/1976 | Carson |
| 4,003,642 | 1/1977 | Vogeley |
| 4,102,564 | 7/1978 | Michael |
| 4,169,663 | 10/1979 | Murr |
| 4,237,383 | 12/1980 | Kosonocky et al. |
| 4,287,410 | 9/1981 | Crane et al. |
| 4,368,959 | 1/1983 | D'Amato |
| 4,373,787 | 11/1980 | Crane et al. |
| 4,387,974 | 6/1983 | Marshall et al. |
| 4,474,186 | 10/1984 | Ledley et al. |
| 4,528,989 | 7/1985 | Weinblatt ............................ 351/210 |
| 4,613,219 | 9/1986 | Vogel ................................. 351/210 |
| 4,648,052 | 3/1987 | Friedman et al. ................... 351/210 |

OTHER PUBLICATIONS

Baloh, R. et al., "Algorithm for Analysis of Saccadic Eye Movements Using a Digital Computer", *Aviation, Space and Environmental Medicine* (May, 1976), p. 253.
Black, J. L. et al., "A Detailed Study of Sequential Saccadic Eye Movements for Normal and Poor-Reading Children", *Perceptual and Motor Skills*, 1984, vol. 59, pp. 423–434.
Pavlidis, G., "Eye Movement Differences Between Dyslexics, Normal, and Retarded Readers While Sequentially Fixating Digits", *American Journal of Opt. 7 Physiological Optics* (1985), vol. 62, 12, pp. 820–832.
WO A1 83/03191, Georgetown University, p. 4, lines 30–32, and p. 7, lines 3–20.
WO A1 83/03341, Ledley et al., p. 4, lines 29–32, and p. 7, lines 4–21.
*Manchester Evening News Article*, Apr. 19, 1978.
Pavlidis, G., "How to Catch His Eye", *Nursing Mirror*, Jan. 31, 1980, vol. 150, pp. 24–27.
Pavlidis, G., et al., *Dyslexia Research and Its Applications to Education*, John Wiley and Sons, Ltd.
Pavlidis, G., "Do Eye Movements Hold the Key to Dyslexia", *Neuropsychologia*, vol. 19, pp. 57–64, 1981.
Pavlidis, G., "Erratic Eye Movements and Dyslexia: Factors Determinig Their Relationsihp", *Perceptual and Motor Skills*, 60, 319–322, 1985.
Pavlidis, G., "Eye Movements in Dyslexia: Their Diagnostic Significance", *J. Learning Disabilities*, vol. 19, No. 1, Jan. 1985.

Primary Examiner—Rodney B. Bovernick
Assistant Examiner—Jay P. Ryan
Attorney, Agent, or Firm—Scully, Scott, Murphy & Presser

[57] ABSTRACT

The specification discloses a diagnostic device and method for detecting various neurological conditions, particularly dyslexia. Eye movement patterns of the subject to be tested are separated into saccadic movement (both progressive and regressive) vergence, pursuit movements and fixations, and the subject's specific eye movement pattern, as evaluated against a specific stimulus, and normal patterns is used for diagnostic purposes. A variety of eye movement detectors is disclosed, together with a sampling means which evaluates the eye position at intervals of less than 10 milliseconds. A data processing means is used to isolate the significant samples and categorizes the retained data samples into the foregoing eye movements. The eye movement patterns are then evaluated against a statistical data base to determine the kind and severity of the diagnosed condition. For example, dyslexic individuals exhibit a high number of regressive saccades, while drug and alcohol impaired individuals are unable follow a stimulus with a pursuit movement, but must rely on a series of short saccades.

28 Claims, 12 Drawing Sheets

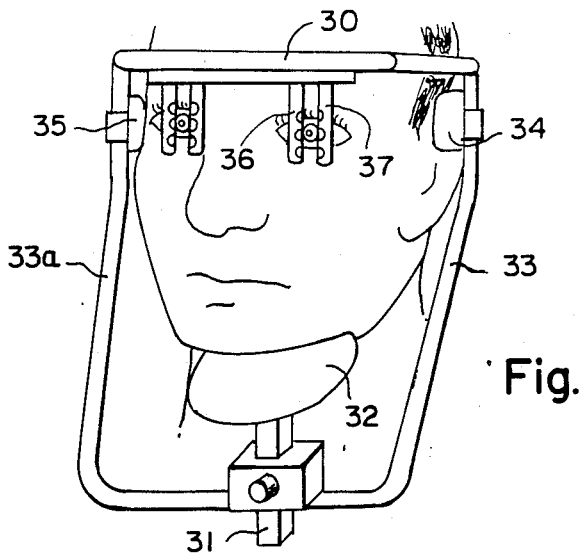
Fig. 3
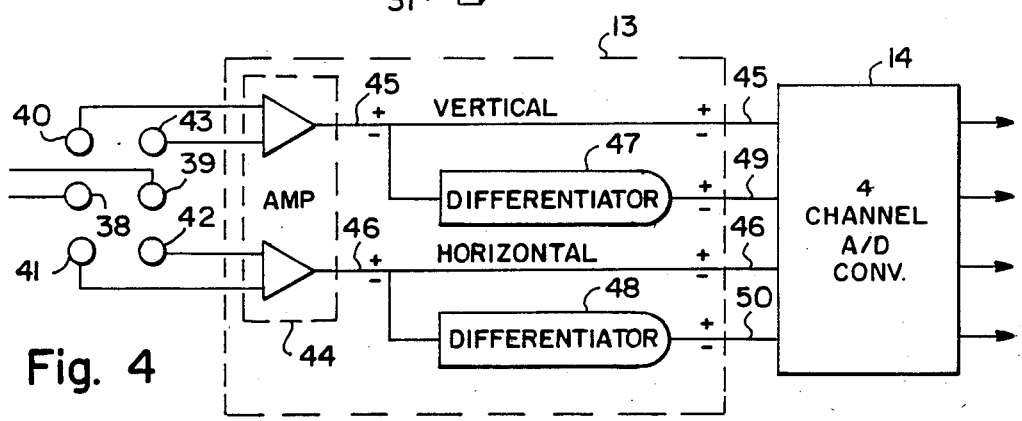
Fig. 4
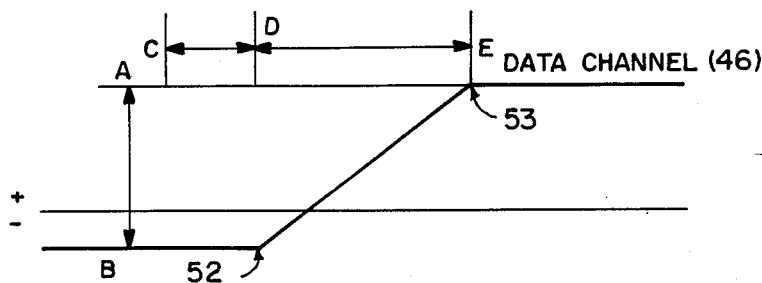
Fig. 5a
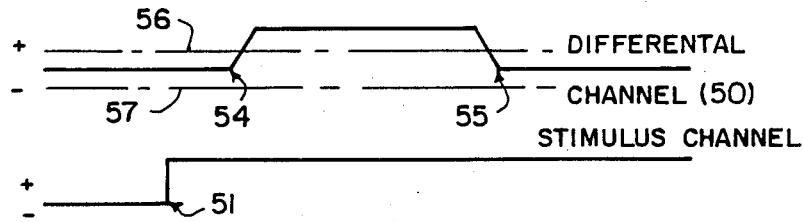
Fig. 5b
Fig. 5c

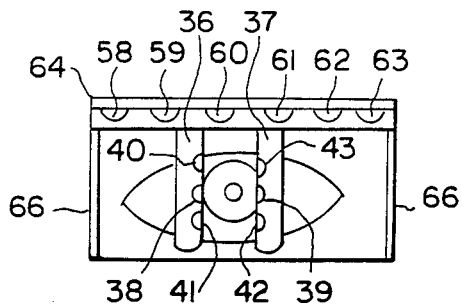
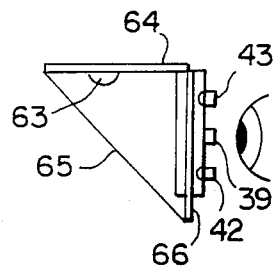
Fig. 6    Fig. 7
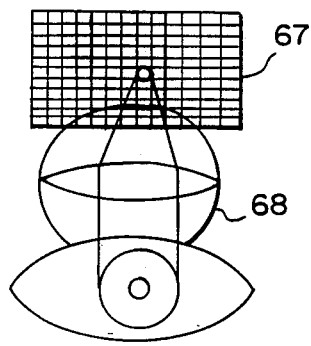
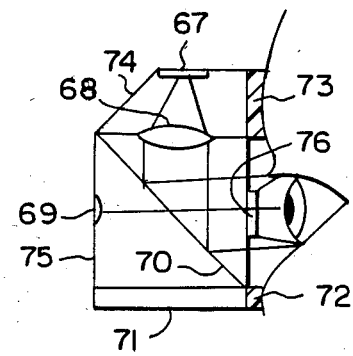
Fig. 8    Fig. 9
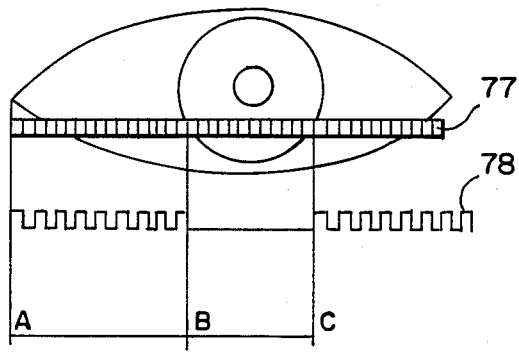
Fig. 10

METHOD AND MEANS FOR DETECTING DYSLEXIA

FIELD OF THE INVENTION

The present invention is a diagnostic method and device for detecting various neurological conditions, including dyslexia. The device is particularly useful for diagnostic tests of dyslexia based on non-reading tasks, which are independent of reading skills.

BACKGROUND OF THE INVENTION

Dyslexia affects the lives of millions of people worldwide and often has devastating psychological, social and educational consequences. It is also one of the most controversial topics in the fields of developmental neurology, psychology, and education. The controversy arises from the incomplete definition of the syndrome of dyslexia and from contradictory theories that surround its etiology.

A major difference between dyslexia and other reading disabilities is that, unlike dyslexia, other categories of reading failure can be predicted on the basis of neurological, intelligence, socio-economic, educational and psychological (motivational, emotional) factors known to adversely affect the reading process. If, for instance, a child has problems in one or more of the above-mentioned areas, he is expected to have reading problems. The extent of the reading disability is determined by the severity and number of factors that are involved.

In contrast, if a child has none of the above-mentioned problems, he is expected to be a normal reader. Children are presently classified as dyslexic when their failure to learn to read cannot be predicted by deficiencies in any of the known causes of poor reading. Psychological, socio-environmental, educational and intelligence factors do not cause dyslexia, although they can contribute to its severity or amelioration. The causes of dyslexia are unknown, and there is substantial disagreement on the definition of dyslexia. Lack of knowledge as to the causes of dyslexia has forced the adoption of definitions based on exclusionary criteria. The diagnosis of dyslexia by the use of exclusionary criteria delays diagnoses by at least 1.5 to 2 years after the beginning of school. This generally results in the development of psychological problems secondary to reading failure, and limited effectiveness of treatment following delayed diagnosis. Furthermore, children presently cannot be unequivocally diagnosed as dyslexics if they are:

(a) psychologically maladjusted prior to beginning schooling;
(b) from a disadvantaged socio-cultural background;
(c) educationally deprived; or
(d) of low intelligence.

It is thus desirable to develop a definition that would identify dyslexics on the basis of positive behavioral, psychological and/or neurophysiological symptoms such as abnormal EEG or evoked potential and/or erratic eye movements. A major advantage of a positive definition of dyslexia is that it would make possible an unequivocal diagnosis in children from disadvantaged socio-cultural and educational backgrounds, as well as in children who are psychologically disturbed or of low intelligence.

Applicant first noted a relationship between erratic eye movements and dyslexia at the University of Manchester, in England. The first known publication of this work was in the Manchester Evening News on Apr. 19, 1978. This article disclosed testing stimulus using a series of lights that flashed from left to right, an eye movement detector and a special video monitor which provided blips which indicated exactly where the subject was looking. According to this article, "It has simply turned out that dyslexics are unable to follow the lights properly *** whereas the control group of normal readers coped without difficulty."

Applicant authored an article entitled "How to Catch His Eye", while at the University of Manchester, that was published in *Nursing Mirror*, on Jan. 31, 1980, Vol. 150, p. 24–27. This article focused on various types of known eye movement detectors, their advantages and disadvantages. This article surveyed direct photographic recording, corneal reflection, contact lenses with mirrors or embedded coils of wire, photo-electric methods detecting the difference in reflectance between the dark iris and the white sclera of the eye and electro-oculography. This article did not apply the reviewed eye movement detectors to a dyslexia device, although it does set forth several desirable criteria that are necessary before an eye movement detector can be used in an apparatus for detecting dyslexia.

Applicant has also edited a book entitled *Dyslexia Research and its Applications to Education* and authored one chapter "Sequencing, Eye Movements and the Early Objective Diagnosis of Dyslexia". This book was published in England by John Wiley and Sons, Ltd. in October of 1981. This chapter does not disclose any specific device or method for analyzing eye movement, but does treat extensively the difference in eye movement patterns between dyslexics and normal or slow readers. The chapter does disclose a sequentially flashing LED display which was used as a visual stimulus for the tests.

U.S. Pat. No. 3,583,794 discloses a direct reading eye movement monitor that uses a pair of photo cells to monitor eye movement, and records the output signal from the eye movement detector on a moving strip chart to provide a graphic representation of the movement of the eyes of the subject.

U.S. Pat. No. 3,679,295 discloses an automatic electronic reading pattern analyzer that uses photo-electric eye movement monitors, and a circuit for analyzing the output of the monitors to provide the analyzed data in readable alpha numeric form. This patent describes an electrical device for distinguishing between normal advancements, fixations, and regressions and return sweeps which it terms the primary or characteristic eye motions of reading. The device, however, does not distinguish between saccade and pursuit movements, and it would appear that its sampling rate is not sufficiently fast to enable it to distinguish between a pursuit and a saccade. At the 100 ms sampling rate, the device would not be able to isolate many of the small eye movements, including the regressive saccade movements which are amongst the primary characteristics of the dyslexic eye movement pattern.

U.S. Pat. No. 4,003,642 teaches the use of a linear data array to facilitate the digital processing of the output of an eye movement detector.

U.S. Pat. No. 4,474,186 discloses a computerized electro oculographic system with a feedback control for the stimuli This patent teaches the use of a computer to analyze the output of an EOG detector and to alter the stimulus administered to the observer in accordance with previously analyzed test results. The analysis performed on the eye movement data, however, is not at all similar to the analysis conducted by applicant's invention. In addition, at the present time, an EOG system is not sensitive enough to reliably detect small eye movements.

U.S. Pat. Nos. 3,842,822 and 3,952,728 to Levinson, et al. disclose various types of dismetric dyslexia screening devices or procedures. Neither of these references, however, analyze the eye movement of the subject.

U.S. Pat. No. 4,102,564 discloses the analysis of eye movements for detecting a neurological condition, particularly nystagmus, which consists of spontaneous oscillatory short and jerky movements of the eyes.

U.S. Pat. No. 4,368,959 discloses an apparatus for and method of testing vision which alters the visual stimulus in order to test for and detect the presence of multiple sclerosis.

U.S. Pat. No. 4,237,383 entitled "High Speed Loading of Output Register of CCD Array System" discloses a semi-conductor array used in an imaging system which has a charge and read cycle sufficiently high to be used as part of an eye movement detector intended for use in the present invention.

SUMMARY OF THE INVENTION

The present invention is a method and means for detecting neurological conditions, and particularly dyslexia. Other neurological conditions that may be detected by use of the present invention include schizophrenia, nystagmus, attentional deficit, inebriation, brain damage, multiple sclerosis, brain dystrophy, as well as the effects of certain drugs, i.e., valium, amphetamines, lithium, etc.

It is an object of the present invention to provide an automated system for determining the existence and severity of dyslexia, etc. for stimulating a predetermined pattern of eye movement in a subject to be tested for dyslexia, etc. detecting the eye movement as a subject observes a stimulus, and analyzing the pattern of eye movement stimulated in the subject by the stimuli. The output of the eye movement detector is sampled at a very high rate of speed, i.e. less than 10 milliseconds and a data collection program is used to isolate the beginning and end of each eye movement, and to discard the intervening data to reduce the amount of data that must be processed. A linearization program is used to linearize the collected data in conformance with the results of a calibration test performed before the recording period, and/or with certain segments of the data. After the data is collected and linearized, it is then analyzed with the beginning and end of each movement serving as fixed reference points. The program then separates the eye movements into fixations, saccadic, vergence movements, pursuit movements (both left and right), and blinks. In addition, specific pursuit or saccade movements, such as a return sweep, or saccadic intrusion in a pursuit task may also be isolated for independent evaluations. Finally, means are provided for displaying the output data in a variety of ways.

It is an object of the present invention to provide a method and means for quickly and affirmatively determining the early presence or existence and severity of dyslexia, and thereby avoiding the delayed diagnosis of dyslexia by the use of exclusionary criteria. It is another object of the present invention to diagnose dyslexia by analyzing a subject's eye movement, isolating the regressive saccades, and computing the percentage of regressive saccades to forward saccades when a forward moving stimulus is being observed. It is another object of the present invention to provide the means for analyzing and quantifying the size of each category of eye movements and time period of fixations, and for isolating short saccades that may occur in dyslexics during fixations. It is another object of the present invention to provide the means for analyzing and quantifying the number, size and duration of return sweeps.

It is still another object of the present invention to determine various neurological conditions such as attentional deficit, hyperactivity, schizophrenia, multiple sclerosis, Alzheimer's, Parkinson's or inebriation by following and analyzing the saccadic and/or pursuit eye movements of a subject observing a moving target. Attentionally handicapped, schizophrenics and inebriated individuals are unable to track the slowly moving target with a pursuit movement of the eye, and must rely on short saccadic movements to locate the moving target. The invention is thus particularly useful for identifying individuals with sequential, attentional, cognitive deficits and impaired motor control. The device is particularly useful for testing individuals' tolerance for alcohol since erratic eye movements are present not only during intoxication, but also in the presence of organic predispositions.

BRIEF DESCRIPTION OF THE DRAWINGS

FIG. 3 is an isometric view of a subject wearing an eye movement detector.

FIG. 4 is a diagrammatic view of the electronic circuitry used in the eye movement detector illustrated in FIG. 3.

FIG. 5a is a diagrammatic representation of the voltage level on one of the data channels for the eye movement detector illustrated in FIGS. 2 and 3.

FIG. 5b is a diagrammatic view of the electrical signal present on one of the differential channels of the eye movement detector illustrated in FIGS. 2 and 3.

FIG. 5c is a diagrammatic view of the voltage level present on the stimulus channel, in its relationship to the data channel and the differential channel.

FIG. 6 is an elevation view of an alternate embodiment of the eye movement detector.

FIG. 7 is a side view of the eye movement detector illustrated in FIG. 6.

FIG. 8 is a diagrammatic view of another alternate eye movement detector using a semi-conductor array.

FIG. 9 is a side view of an eye movement detector utilizing a semi-conductor array.

FIG. 10 is a diagrammatic view of an alternate embodiment of the eye movement detector utilizing a linear diode array.

DETAILED DESCRIPTION OF THE PREFERRED EMBODIMENT

Eye movement efficiency develops almost in parallel with the reading process. The importance of the use of eye movements as an objective tool for the study of the individual components of the reading process is further enhanced by the fact that the performance of our eye movements is beyond conscious control while observing a stimulus.

Reading skills develop gradually, improving in precision and speed over the years. They develop in parallel with, and are clearly reflected in the patterns and characteristics of the reader's eye movements. Most of that development occurs during the first 3 to 4 years of schooling. About two-thirds of the total development of a reader's eye movements that occurs between first grade and college level has been achieved by 10 years of age. The overall developmental pattern for eye movements suggests that during both reading and visual search, an inverse relationship exists between age and duration of fixation, and the number of forward and regressive eye movements, i.e., the older the child, the shorter the duration of fixation. Usually, a shorter fixation is an indication of a faster information processing time or word recognition time.

Regressions during reading have been partly attributed to the problems that the reader has in comprehending the material, to large forward saccades which overshoot the intended subject, and to semantic control and inference making.

Applicant has discovered that dyslexics exhibit erratic eye movements during reading. The main characteristics of erratic eye movements are the excessive numbers of eye movements, particularly regressions, which often occur two or more in succession. The sum of amplitudes or individual amplitudes of regression can be larger than the preceding forward saccade This is very different from patterns shown by advanced, normal, and non-dyslexic retarded readers, who make singular regressions of the same or smaller size than the preceding forward saccade.

Figure 11A:
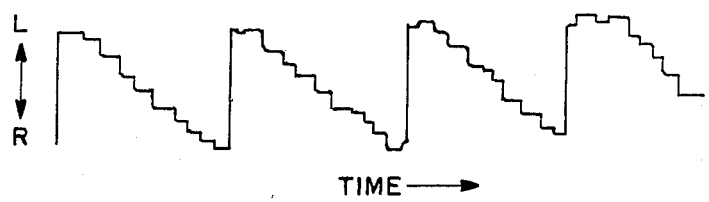
FIG. 11a is a strip chart illustrating the left to right eye movement pattern of a normal reader.

Other characteristics of dyslexic eye movements include great variability in size and duration The overall impression given by erratic eye movement pattern is irregularity, idiosyncratic shape and the lack of a consistent repetitive pattern line after line As can be seen in FIG. 11a a strip chart pen recording of a normal reader's eye movement resembled the shape of a staircase. Each staircase represented in FIG. 11a represents a line of text. The longer the time spent to read the line, the longer the staircase The first top "step" represented the first fixation at the beginning of the line, while the last bottom "step" represents the last fixation at the end of the line. Forward eye movements (L-R) go from top to bottom, while regressions (R-L) had the reverse direction.

CASE STUDIES

Applicant has conducted case studies in which the eye movement patterns of dyslexics, other retarded readers, normal and advanced readers are compared. In selecting the research and diagnostic criteria for dyslexia, care was taken to exclude any known factors that could potentially be a primary cause of a reading problem. Another aim of the criteria was to quantify as many qualitative factors as possible, e.g., educational opportunities.

Guided by these concepts, the following factors were taken into account in establishing the research diagnostic criteria for dyslexia. In summary, they were average or above average IQ, at least 1.5 years retarded in reading if below 10 years of age or 2 years reading retardation if above 10 years of age, normal visual and auditory acuity, advantaged socio-economic background, no emotional or motivational problems prior to beginning reading, no overt physical handicaps and adequate educational opportunities. Children who fulfilled all of these criteria were included in the dyslexic group. Among other factors, the control group of advanced and normal readers as matched to the dyslexics for chronological age, while the retarded readers were matched for both chronological and reading ages.

While the children were reading, their horizontal and vertical eye movements were recorded by means of a highly sensitive, non-invasive photo-electric method, modified by applicant to suit the experimental requirements. The sensitivity of the method was enough to distinguish fixations of different letters of the same word.

The results of this study have shown that the number of forward and regressive eye movements was significantly higher in dyslexics than in matched retarded, normal and advanced readers. These findings replicated the applicant's earlier studies comparing dyslexics with matched normal readers.

The characteristic that again stood out was the excessive number of regressions made by dyslexics. And in a number of cases, the regressions occurred in succession, in clusters of two or more, producing an irregular erratic pattern that can be seen in FIG. 12a.

Figure 12A:
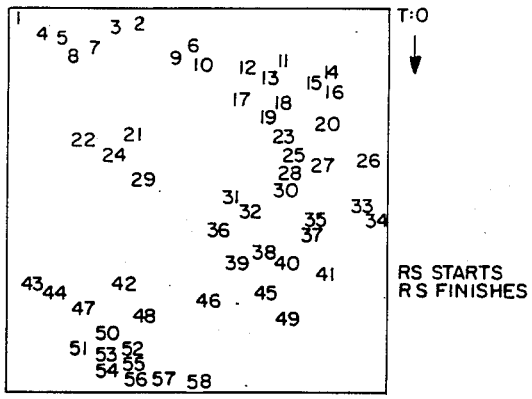
FIG. 12a is a computer printout illustrating the relative eye position of a dyslexic reader while reading two lines of text. The vertical dimension represents time.

FIG. 12a represents the relative eye positions as a dyslexic reader attempted to read a line of text. The horizontal location of the numbers represent the position of the fixation in relation to the line, while the consecutive numbers reflect the number of their occurrence.

Figure 12B:
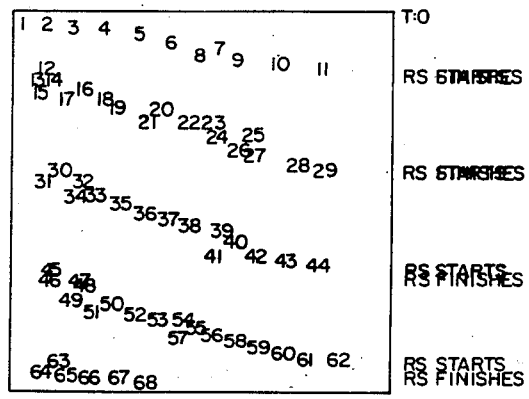
FIG. 12b is a similar computer printout illustrating the relative eye position of a normal reader while reading five lines of text.

As can be seen in FIG. 12b, a normal reader read each line with regular left to right eye movements, interrupted by small regressions. A return sweep followed the conclusion of each line of text.

The dyslexic eye movement recorded in FIG. 12a, however, made 41 disorganized eye movements to read one line and needed two large eye movements to reach the beginning of the next line of text.

To summarize the results, the dyslexics made significantly more regressive movements and fixations than each of the other three control groups when each child read text appropriate to his/her reading age. Retarded readers made significantly more regressions than normal readers, and they in turn made significantly more than advanced readers. Dyslexics made significantly more regressions than normal readers even when dyslexics read the easy text and normal readers, the difficult text.

In addition, the percentage of regressions of the total number of eye movements was compared for each group. The dyslexics were still found to have significantly more regressions than other readers, including retarded readers. However, there was no significant difference between the non-dyslexic groups. This finding suggests that advanced, normal and retarded readers belong to the same contingent, while dyslexics were a distinctly different group.

Figure 11B:
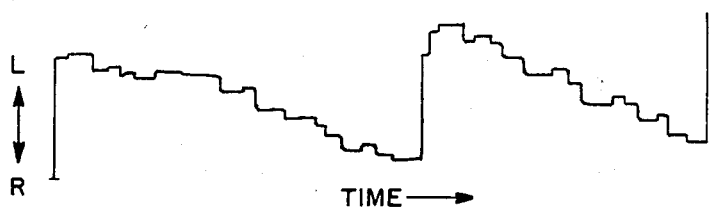
FIG. 11b is a strip chart illustrating the left to right eye movement pattern of a slow reader.
Figure 11C:
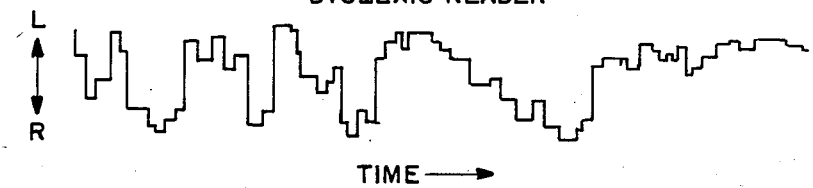
FIG. 11c is a strip chart illustrating the left to right eye movement of a dyslexic reader.

FIGS. 11a, 11b and 11c represent, respectively, the eye movement patterns of normal, slow, and dyslexic readers. The eye movement of the slow reader illustrated in FIG. 11b illustrates a more erratic pattern than those of the normal reader, illustrated in FIG. 11a, and the length of time the slow reader took to complete a line of text was almost twice that of a normal reader. The general pattern of the slow reader, however, was substantially the same as the normal reader, with only a few extra regressions.

The eye movement pattern of the dyslexic reader, as illustrated in 11c, however, shows an erratic pattern having a large number of regressive eye movements, short fixations and frequent large saccade movements jumping back and forth from the beginning to the end of the line of text.

The results of the study prove conclusively that dyslexics' erratic eye movements are not a reflection or symptom of their reading problems. If the eye movements were associated with reading problems, the eye movements of the dyslexics and the matched retarded readers should have been similar because they were equally retarded in reading. On the contrary they were found to be significantly different. Secondly, providing an easier text did not normalize the dyslexics eye movement patterns. Further, the normal reader's eye movements did not become erratic even when they read a difficult text.

Figure 11D:
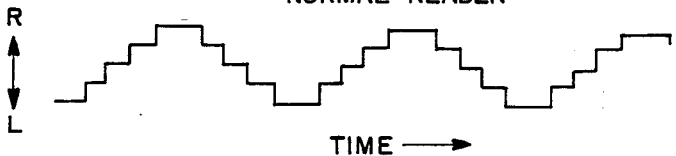
FIG. 11d is a strip chart illustrating the eye movement of a normal reader following a sequentially moving light visual stimulus.

In a related case study, applicant compared 12 dyslexic readers and 12 matched normal readers. They were tested in a non-reading task that simulated the sequential scanning from the beginning to the end of the line that occurs during reading. Words were replaced with lights. Children were asked to follow, as quickly and as accurately as possible, five lights that were equidistantly spaced in a horizontal array. These were illuminated sequentially and each stayed lit a second—except the two extreme lights were lit for two seconds. The process started with the extreme left light and each was lit in turn until the extreme right light was lit, then the reverse sequence was completed. As the subjects followed the lights, their eye movements were recorded. The eye movement pattern of a normal reader following the progression of illuminated lights is illustrated in FIG. 11d.

Figure 11E:
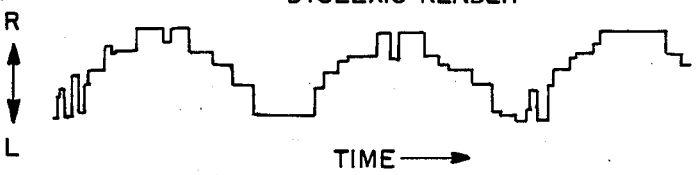
FIG. 11e is a strip chart illustrating the eye movement of a dyslexic reader following a sequentially moving light visual stimulus.

The eye movement pattern of a dyslexic reader following the same progression of lights is illustrated in FIG. 11e. As can be seen by comparing FIG. 11d with FIG. 11e, the dyslexic reader, unlike the normal reader, made many regressions and forward movements, similar to those made in the reading patterns illustrated in FIG. 11c. The dyslexic reader made far more small adjusting eye movements and in 4 out of the 5 two-second fixations, he broke the fixations into smaller ones with small saccades in the middle of the fixation. The dyslexic also showed a tendency to incorrectly anticipate the onset of the next light, which characteristic sharply contrasts with the normal readers ability to consistently and accurately fixate on the lights.

Dyslexic and retarded readers had highly significant differences in almost all eye movement variables, whereas the performance of retarded readers was not significantly different from that of normal or advanced readers. There was little overlap between dyslexics and all other readers in the number of regressions. As illustrated in the following Table I, the dyslexic made a similar percentage of regressions while following the sequentially illuminated lights as they did during reading the easy text. On the other hand, as expected, the percentage of regressions for retarded, advanced and normal readers dropped significantly from reading to the non-reading task because there was no high level information processing involved in the light-following task.

TABLE 1

Percent of Regressions While Reading and While Following Lights

| Groups of Readers | % Regressions Reading at Reading Age | % Regressions Following Lights |
|---|---|---|
| Dyslexics | | |
| x | 34.0 | 29.9 |
| SD | 8.0 | 8.1 |
| Retarded Readers | | |
| x | 22.9 | 9.8 |
| SD | 8.3 | 10.0 |
| Normal Readers | | |
| x | 20.8 | 6.8 |
| SD | 6.8 | 9.4 |
| Advanced Readers | | |
| x | 18.0 | 8.4 |

TABLE 1-continued

Percent of Regressions While Reading and While Following Lights

| Groups of Readers | % Regressions Reading at Reading Age | % Regressions Following Lights |
| --- | --- | --- |
| SD | 8.4 | 11.4 |

The foregoing results illustrate that dyslexics, unlike other non-dyslexic readers, have a primary problem independent from reading. The non-dyslexic groups were indistinguishable from each other on the basis of eye movement characteristics.

The main conclusions that can be drawn from the eye movement studies to date are the following:

1. The dyslexics' erratic eye movements found during reading are not solely caused by the problems they have with reading. In fact, they are relatively independent of the reading problem.
2. The results of the non-reading tasks further demonstrate that dyslexics' erratic eye movements are due to a brain malfunction(s) yet to be determined.
3. The comparison of dyslexics, advanced, normal and retarded readers shows that eye movement patterns and characteristics in the non-reading "lights" test can differentiate dyslexics from other groups of readers.

MEANS FOR DETECTING DYSLEXIA

Figure 1:
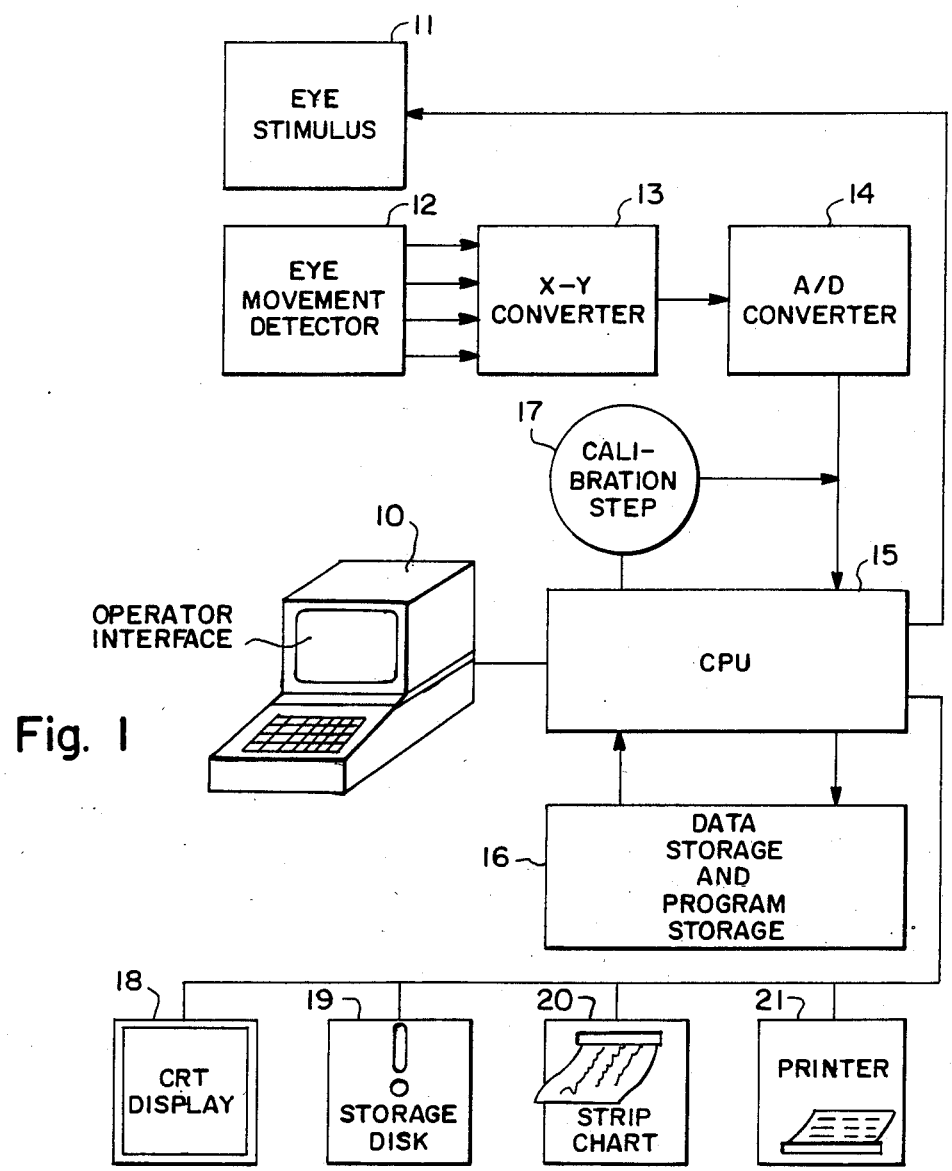
FIG. 1 is a diagrammatic view of a data processing system for implementing the present invention.

An automated system for determining the existence of dyslexia is disclosed in FIG. 1. This system includes an eye stimulus means 11 for stimulating a pre-determined pattern of eye movement in a subject to be tested for dyslexia. As will be hereinafter described, this means may be a series of flashing diodes, a target illuminated on the face of a CRT tube or other electronic display, means for displaying text to be read, or a projected light spot on a wall or other screen. The system also includes an eye movement detector 12 for detecting eye movement in a subject observing the eye stimulus means. The eye movement detector provides an electrical output signal in response to the movement of the subject's eye. A variety of eye movement detectors may be used, e.g., EOG, photoelectric corneal reflection, and video camera methods. When a diode array, such as that illustrated in FIGS. 3 and 4 is used, an x-y converter 13 is used to convert the DC diode signals from the 4 diodes into electrical signals that are representative of the x and y positions of the eye. This will be further described in connection with the description accompanying FIGS. 3 and 4. After the eye movements have been converted to DC signals, an analog to digital converter 14 is used to translate the analog signals into digital signals for use by the processing means 15. The processor means 15 receives the electrical output signals and includes a means for sampling the output signal at intervals of less than 10 milliseconds to obtain a series of successive eye positions over time. The processor includes a data collection program that will convert the incoming digital values into data representing eye positions over time, and an analysis program for analyzing the data and categorizing the eye movements into micromovements, saccade movements, pursuit movements, convergent-divergent movements, fixations and blinks. The data collection and data analysis programs are stored in memory means 16, along with the data derived by the processor means, from the data collection program. Further calibration of the data can be achieved by re-analyzing specific parts of the data.

After the eye movement detector has been mounted on a subject to be tested, the relative position of the detector with respect to the subject's eye is calibrated, and this automated calibration is subsequently used to linearize the data as indicated at step 17 as it is collected, but before it is analyzed.

An operator interface 10, which would generally include some type of keyboard means, and some type of output display means, is used to interact with the processor means 15 to select the various test parameters, to initiate the testing and data collection and to initiate the analysis of the data. In addition, the operator may select one or more of a variety of output means, including an optical display on an LCD screen, a CRT 18 or other electronic display, recording the data or the analyzed data for future use on a removeable storage disk 19 (such as a magnetic floppy or removeable laserdisk), or providing an intermediate output of the eye movements by virtue of a strip chart recorder 20. In addition, the operator may either output the data directly with printer 21 or may compare the analyzed data with data previously collected in a statistical data base to indicate the existence and severity of dyslexia, or other neurological conditions. Both the individual test output, and an indication of the relative severity of the condition under investigation can be printed out on printer 21.

Figure 2:
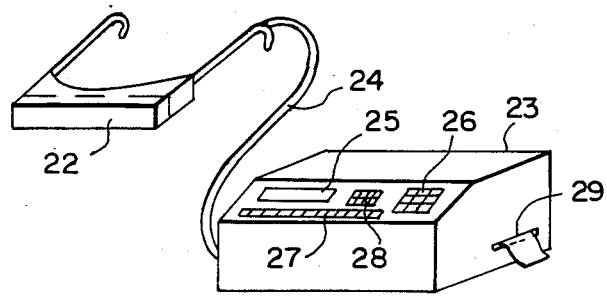
FIG. 2 is a diagrammatic view of another embodiment of the present invention.

While the testing done has been conducted on a data processing system using separate components, it is believed that the preferred combination for practicing the invention would include an integrated eye stimulus and eye movement detector, a single "black box" with a key pad, a display means and a printer for recording the output of the test. The output would include an indication of the existence and severity of dyslexia, and suggestions for further testing, possible causes, and appropriate methods of treatment. Such a device would be highly portable and could be moved from classroom to classroom or clinic to clinic, and could be used by non-medical personnel with a minimal amount of training. Such a device is conceptually illustrated in FIG. 2. As illustrated, the integrated eye stimulus and eye movement detector 22 is connected to the means for detecting dyslexia 23 by means of electrical cord 24, or by a transmitter/receiver not shown. The means includes an alpha numeric display panel 25, a numeric key pad 26, a series of function keys 27 and a set of status indicators 28 for communicating with the operator The output of the device is provided by means of printer/plotter 29.

The eye movement detector used in deriving the experimental data is depicted physically in FIG. 3, and electronically in FIG. 4. As illustrated in FIG. 3, the eye movement detector includes an adjustable frame 30. The frame 30 is used in conjunction with a head stabilizing means 31 which includes a chin pad 32, extension bars 33, 33a and adjustable head alignment guides 34 and 35. The eye movement detector includes a 4-diode array which is mounted in and suspended from a pair of lucite tubes 36, 37 which bend downward in front of the subject's eye, and provide a space for the subject to view the eye stimulus means. The same eye movement detectors can be mounted on the headrest via a rod arrangement that allows eye movements of six degrees of freedom.

As illustrated in FIG. 4, the eye movement detector includes a pair of photo diodes 38 and 39 for illuminating the eye. While many types of illuminating means may be used, infrared illumination is preferable inasmuch as it is non-invasive to the visual test, and the narrow spectral width of the infrared illumination makes it easily separable from other interfering sources of energy that may reach the eye. Photocells 40–43 are directed to the opposite boundary regions between the dark iris and the white sclera established by the eye when looking in a straight forward direction. They measure the reflected light at each boundary as it changes with horizontal or vertical movements of the eye. The photo diodes 38 and 39 may be steady state or pulsed illumination and remain on for the duration of the test. Pulsed illumination is preferable because it makes the system much less sensitive to ambient illumination.

The output of photo-detectors 40–43 is connected to an x-y converter 13 which is conceptually illustrated with integrating amplifier 44 and differentiators 47 and 48. The output signal of diodes 40 and 43 is added for the vertical signal, and the output signal is provided as a smooth DC signal on line 45 which is a function of the vertical position of the eye, e.g., with a positive voltage reflecting an upward movement and a negative voltage reflecting a downward movement. Likewise, the output of photo-detectors 41 and 42 is subtracted by amplifier 44 to obtain the relative horizontal position of the eye. A smooth DC signal is provided on line 46 which is positive when, for instance, the eye is directed to right of center, and negative when the eye is directed to left of center. Differentiators 47 and 48 provide a differentiated signal on lines 49 and 50. Differentiators 47 and 48 provide a changing output signal only when the output voltage present on lines 45 and 46 is changing. When the output signal is constant, differentiators 47 and 48 also provide a constant output signal. The output signals present on lines 45, 46, 49, and 50 is then directed to a four channel analog to digital converter 14 which digitizes the DC output signals.

The respective relationship between the output signal on the data channel, the output on the differentiated signal channel, and the electrical signal on the stimulus channel is illustrated in FIGS. 5a–5c. As illustrated in FIG. 5c, an event 51 is initiated along the stimulus channel by energizing one on the photodiodes in the eye stimulus means. Alternately, the signal present on the stimulus channel could be a single pulse or data word from the processing means indicating that a signal had been sent to the video display to display a new target on the CRT screen. Approximately 0.2 seconds (normal reaction time) after the stimulus is energized, eye movement begins in the subject as indicated at point 52 in FIGS. 5a and c. The DC signal present on line 50 prior to the stimulus was slightly negative, and in response to the stimulus, the eye moved horizontally to the right to the location of the new stimulus creating a rise A-B in the DC voltage as illustrated in FIG. 5a. The eye movement ends at point 53 and begins a fixation on the new stimulus. Since the sum or difference of the signals from the photodiodes do not change when the eye is static, the relative voltage level present on the data channel remains constant when the eye is fixed.

FIG. 5b depicts the signal that is present on the differentiated channels 49 or 50. When the eye is fixed, and the output signal on the data channel is constant, there is also a constant signal on the differentiated channel 50. As the eye movement begins at point 52, the differentiated channel indicates a change in voltage level on data channel 46 by means of the differentiated output signal 54. The differentiator 48 continues to generate a signal so long as the signal on the data channel is changing. When the eye reaches fixation, as indicated at point 53, the signal of the differentiated channel again drops to zero as indicated at 55.

As will be hereinafter described in more detail, the system uses noise limits to separate random noise from the initiation of an eye movement. One of the noise limits is graphically illustrated in FIG. 5b as voltage limits 56 and 57. The said noise limits are calculated during calibration and are passed on to the analysis program.

The use of data channels 45 and 46 and the differentiated channels 49 and 50 will be hereinafter described in more detail with respect to FIGS. 14 and 15.

It is apparent that a wide variety of eye movement detectors will work with the present invention, provided the accuracy and sensitivity is capable of distinguishing between the various types of small eye movement. Such an eye movement detector should have high accuracy, and be capable of determining the eye position resulting from a few minutes of arc in eye motion. It should also have high sensitivity, and be able to note when the eye position changes by a few minutes of arc. It should be capable of providing high-time resolution, on the order of 1 millisecond (1 ms) or better. While a system sampling at rates upwards of 7 to 10 ms may be able to distinguish between saccade and pursuit movements, it is preferable to sample at a higher rate, preferably at least 1 ms. Finally, the eye movement detector should have a wide angular measurement range of ±30° to 40° horizontal and ±20° of vertical arc.

An improved eye movement detector of the type illustrated in FIG. 3 having a visual stimuli combined therewith is illustrated in FIGS. 6 and 7. In these figures, the light emitting diodes 38 and 39 and the photo-detectors 40–43 are mounted in clear lucite columns 36 and 37 as previously indicated with respect to FIG. 3. The visual stimuli comprises light emitting diodes 58–63 which are mounted on support means 64, and are reflected to the subject on a half-silvered mirror 65 which extends from mount 66 to support member 64. It has been found advantageous to provide at least 5 to 7 diodes or visual stimuli spaced apart by approximately 2° to 6° of arc, with a preferred spacing of 4° of arc so that the total sweep of eye movement is between 20° and 30° in the horizontal plane.

The use of diodes provides a visual stimulus or test for dyslexia that is free of cultural, intelligence, language, socio-economic and educational barriers. The test is not affected by relative intelligence or reading ability, and is equally applicable to normal readers, advanced readers and retarded readers. The subject is instructed to hold the eyes on the center of the light that is lit, wait for it to move and then move the eyes to the new light as quickly and as accurately as possible. By sequentially illuminating the LEDs, the subject will be tested for oculomotor control (control of saccadic movements), automated-sequencing, prediction/synchronization, the ability to alternate between two "time sets", and the ability to concentrate or fix the eyes at a specific point. A similar test with diodes resulted in the normal reader pattern and dyslexic reader pattern illustrated in FIGS. 11d and 11e.

During testing, the 7 LEDs will be sequentially illuminated, one at a time, and each will be lit for one second, except that the central and the two extreme LEDs will be lit for 2 seconds. The sequence begins at the extreme left, and each light will light in turn until the extreme right LED is illuminated. Each test cycle lasts for approximately 10 seconds, and each subject will follow the LEDs for at least 3 cycles.

If it is desired to test only the oculomotor control of the saccadic movement of the eyes, the LEDs may be randomly illuminated. In addition, if it is desired to test the ability to fixate, a period of fixation may also be randomly changed between 1 and 2 seconds. If it is desired to test oculomotor control along with an automated sequencing test, then all LEDs may be synchronously illuminated, and the subject told to move as quickly and accurately as possible from one LED to the next.

As indicated previously with respect to FIGS. 11d and 11e, a non-dyslexic person will have little difficulty following the LEDs in the foregoing sequences. A dyslexic reader, on the other hand, will not be able to follow the LEDs accurately, will have many regressive saccades, and the fixation periods will be broken by short saccades as illustrated in FIG. 11e.

The eye movement detector may also utilize semiconductor or diode arrays to accurately determine the position of the eye. As conceptually illustrated in FIG. 8, the relative position of the iris is focused upon a diode array 67 by means of an optical system 68. Diode array 67 may be a photo diode array, a CCD array or a CID array that is integrated with its own sweep and charge circuits, and accumulating registers for providing an output location of the iris of the eye as x-y coordinate values. The use of a diode array is illustrated in FIGS. 8 and 9 wherein the sclera of the eye is illuminated by photo emitting diode 76, and the illumination reflected upwardly by a half-silvered mirror 70 to an optical system 68 which reduces the relative image size of the iris and focuses it upon diode array 67. The visual stimulus 58-63 illustrated in FIG. 6 is diagrammatically shown at 69 in FIG. 9. The diode array 69 is mounted upon support 75 which bridges support 71 and housing member 74. The entire apparatus is strapped to the subject's head and cushioned by means of pads 72 and 73 or can be placed on a headrest.

An alternate eye movement and pupil size detector is illustrated in FIG. 10 where a linear diode array 77 is positioned immediately adjacent the eye, as illustrated in FIGS. 6 and 7 by the position of photo-detector 42. The sclera of the eye is illuminated by one or more light emitting diodes and the boundary between pupil and the iris and the iris and the sclera is detected by the diode array 77. Each individual diode, when scanned, will provide an output pulse when illuminated by the reflective sclera as indicated at 78. The darker iris will not reflect as much light, and the pulses at that location will be absent. The exact center of the eye can be calculated as:

$$Ep = (b - a) + \frac{c - b}{2}$$

As indicated previously, the eye stimulus may also take the form of targets that are illuminated on a CRT, CCD display or any other form of electronic display device, or as light spots that are projected upon a screen. The exact mode of stimulus is relatively unimportant, provided relative motion between the subject's head and the visual stimulus can be avoided. Rotational movement of the head will create problems in the calibration and linearization of the data as will be hereinafter discussed. For this purpose, when using an external stimulus, a head support of the type illustrated in FIG. 3 is desirable.

Figure 13A:
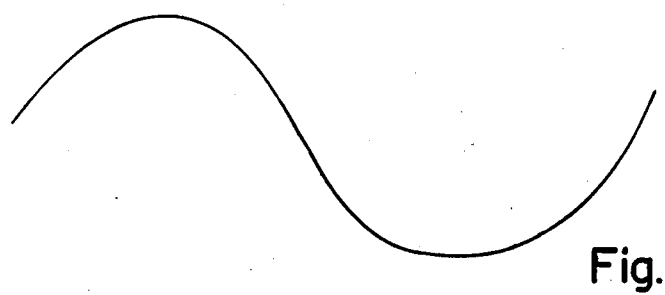
FIG. 13a is a diagrammatic representation of the pursuit eye movement following a target moving in a sinusoidal pattern.
Figure 13B:
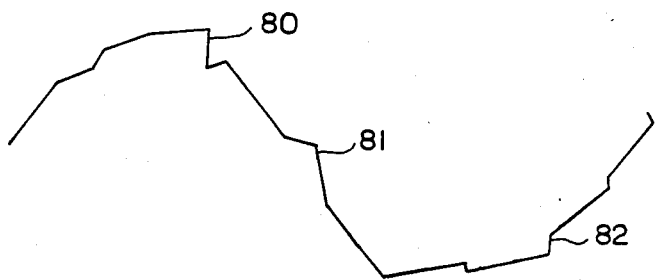
FIG. 13b is a diagrammatic representation of the eye movement of a schizophrenic, attentionally handicaped, hyperactive or inebriated subject while attempting to follow a target moving in a sinusoidal pattern.

With a slowly moving target on a video monitor or CRT, or a projected light spot, it is possible to create a sinusoidal pattern as illustrated in FIG. 13a. The speed of the target should be between 2° and 7° or higher of arc per second. The sinusoidal test illustrated in FIG. 13a has been found useful in identifying schizophrenics, primary attentional deficit, multiple sclerosis, Parkinson's disease, Alzheimer's disease, the effect of drugs (psychotropic drugs, e.g., valium, and stimulants etc...) and the effects of alcohol. These groups are unable to track a moving target with a pursuit eye movement. These subjects use a series of corrective saccades as illustrated in FIG. 13b to track the moving target with many over-corrections as illustrated at points 80-82 when the eye under- or over-shoots the path of the target and must immediately compensate with another short saccade. Some subjects with a low tolerance to alcohol lose motor control far below the legal limit. This test would improve the test for alcohol impairment by identifying those individuals whose attentional motor controls were truly impaired, as opposed to those with a certain percentage of alcohol in the bloodstream, but no impairments.

DATA COLLECTION PROGRAM

Data collection is a step in the gathering and analyzing procedure that allows the method and means to vastly simplify the number of calculations necessary to categorize eye movements. Three types of data collection programs are illustrated in FIGS. 14, 15 and 15a, respectively. The programs illustrated in FIGS. 14, 15 and 15a are particularly adaptable for use with slow microprocessors, while the program illustrated in FIG. 15 can also benefit from larger or faster processors with higher operating speeds.

Figure 14:
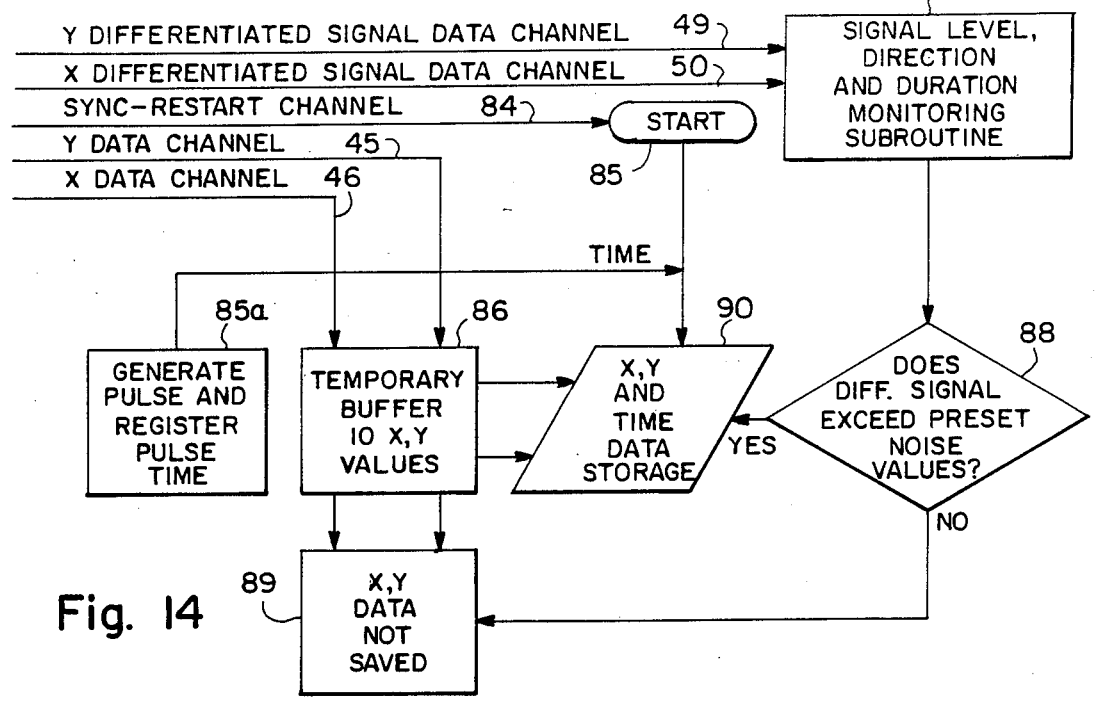
FIG. 14 is a system flow chart illustrating a data collection program for use with the eye movement detector illustrated in FIGS. 3, 4, 6 and 7.

As illustrated in FIG. 14, the data channels previously described with respect to FIGS. 3 and 4 are used, with the x-data channel 46 and the y-data channel 45 provided to temporary buffer 86. The x differentiated signal 50 and the y differentiated signal data 49 are provided to an evaluation sub-routine 87. At the beginning of data collection, a time signal is initiated, and sampling begins as indicated at step 85. In addition, a pulse is generated in step 85a for each change in the stimulus status. The time of the stimulus status change is sent to the data storage step 90, where the stimulus status indicator, the time data, and the x-y period are stored. Sampling may take place in the microprocessor, or it may be a function of the analog to digital converter 14 which provides a digital signal at every desired sampling interval. As indicated previously, it is desirable to sample at approximately 1 milli-second intervals (1 ms). A temporary buffer is established as indicated at 86 to hold 10 consecutive x-y positional values. At each interval, a new value is read into the buffer, and one is read out as indicated at step 89. The sub-routine 87 is concurrently monitoring the differentiated signal data channels 49 and 50 for signal level, signal duration and signal direction. If the differentiated signal exceeds a predetermined noise level, for a predetermined duration (approximately 3 ms) and occurs in the same direction, it is presumed that an eye movement has begun.

As indicated at evaluation 88, if the differentiated signal exceeds the noise parameters established for level, duration, and signal direction, then the program saves the 10 values of x-y values that are presently in the temporary buffer 86, together with the time data that has been simultaneously entered along the time channel. This program thereby records 5 data points on either side of the beginning of the eye movement together with the time at which the eye movement began. During periods of fixation, the differentiated signal will drop to zero and the x-y data will not be saved. Only the data points at the beginning and end of each eye movement or blink are saved. In a pursuit eye movement test, the beginning, end and any change in direction that exceeds 0.1° is saved.

Figure 15:
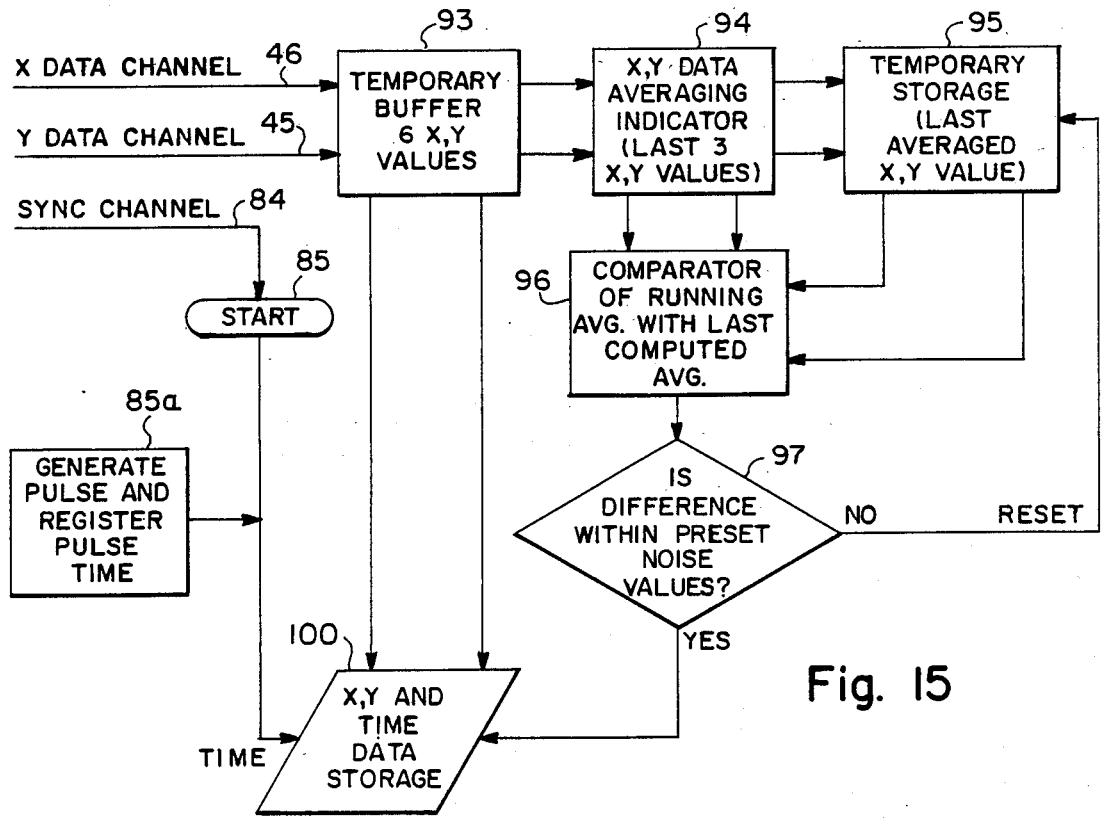
FIG. 15 is a system flow chart of an alternate data collection program for use with an eye movement detector as illustrated in FIGS. 6–10.
Figure 15A:
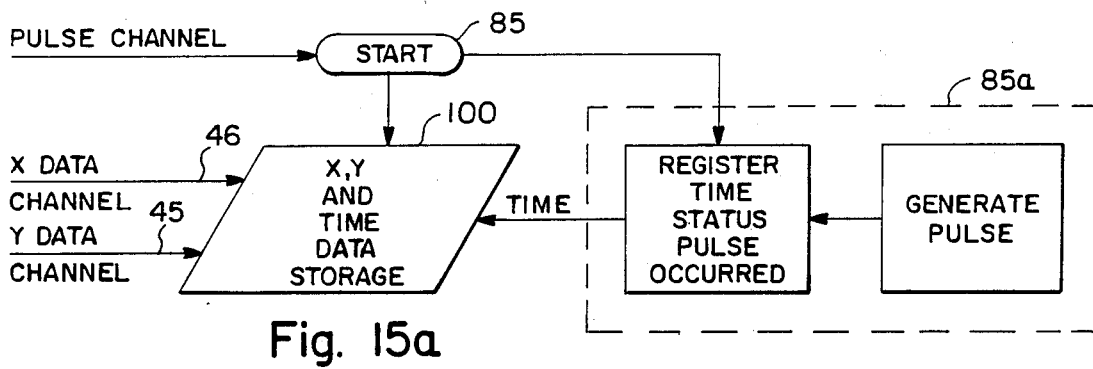
FIG. 15a is a system flow chart illustrating a real time data collection program for storing all values.

An alternate data collection program is illustrated in FIG. 15. This program is particularly adapted for faster or larger microcomputers that are able to continuously calculate a running average of the data on the data channels. It is also appropriate for integrated circuit diode arrays that have a diode array or CCD array that has the charge sweep and accumulating buffers mounted on the same integrated circuit as the diode array. These integrated circuits provide a digital output of the x and y coordinates of the position of the eye and of the size of the pupil.

At the time data collection is initiated, sampling is begun at a time line established at step 85 as previously indicated with respect to FIG. 14. Step 85a provides a pulse at each change in stimulus status which is recorded in step 100 with the x-y data and time data at the time of the pulse. Alternatively, the sampling period may be a function of the A/D converter, if used, or the clock and sweep rate of the IC circuitry associated with the diode array.

At the initiation of the collection program, a time channel is also established for future use in computing the duration of the fixation and the speed of the eye movement. The positional data present on the x and y data channels 45, 46 are accumulated in temporary buffer 93. In continuously averaging the data, a running average is computed as indicated at step 94. At the end of each calculation cycle, the last average value is stored in temporary storage 95. Immediately upon completion of the new running average, the previous running average is compared with the new running average indicated in step 96. If the difference does not exceed the noise parameters established by the program, the temporary store 95 is reset as indicated in step 97, and a new running average is computed as indicated at step 94. If the difference exceeds the noise parameters previously established, then the x-y data is saved in step 100 with its respective time data, in storage device 16. This method of data collection provides approximately 2 data points at each change in direction of the eye movement.

The data collection routines illustrated in FIGS. 14 and 15 vastly simplify the amount of data required to be analyzed. For a typical test involving 7 diodes with the first, middle and end diode being illuminated for 2 seconds, and the intervening diodes being illuminated for 1 second, approximately 23 fixations would be recorded in a normal test, with 22 eye movements therebetween. This test would consume approximately 30 seconds of total time. By recording only the beginning and end points of the eye movements, ideally it is necessary to save only 60 data points. However, more eye movements are normally saved than those that finally satisfy all the eye movement criteria. Still, the number of data points saved will be many times fewer than the 30,000 data points that would be accumulated if the entire output of the test were stored, as illustrated in FIG. 15a. FIG. 15a represents a sub-routine for storing all sampled data on the x and y channels with the accompanying time data, with like numerals indicating similar program steps to the steps previously described with respect to FIGS. 14 and 15.

DATA ANALYSIS

The function of the data analysis program illustrated in FIGS. 16a–16e is to take the collected data points that mark the beginning and the end of each eye movement or blink, determine what type of eye movement occured, and calculate the parameters which describe that eye movement or blink. The major eye movements include the saccadic (the fast jerky movements used during reading and visual scanning) movement, the fixation, the blink, the pursuit (the slow movements used for tracing a slowly moving object in a stationary environment), and the vergence eye movement which is used for looking with both eyes at near or distant objects. This program analyzes the data and classifies a respective movement in one of these categories, and computes the parameters of each movement.

Figure 16A:
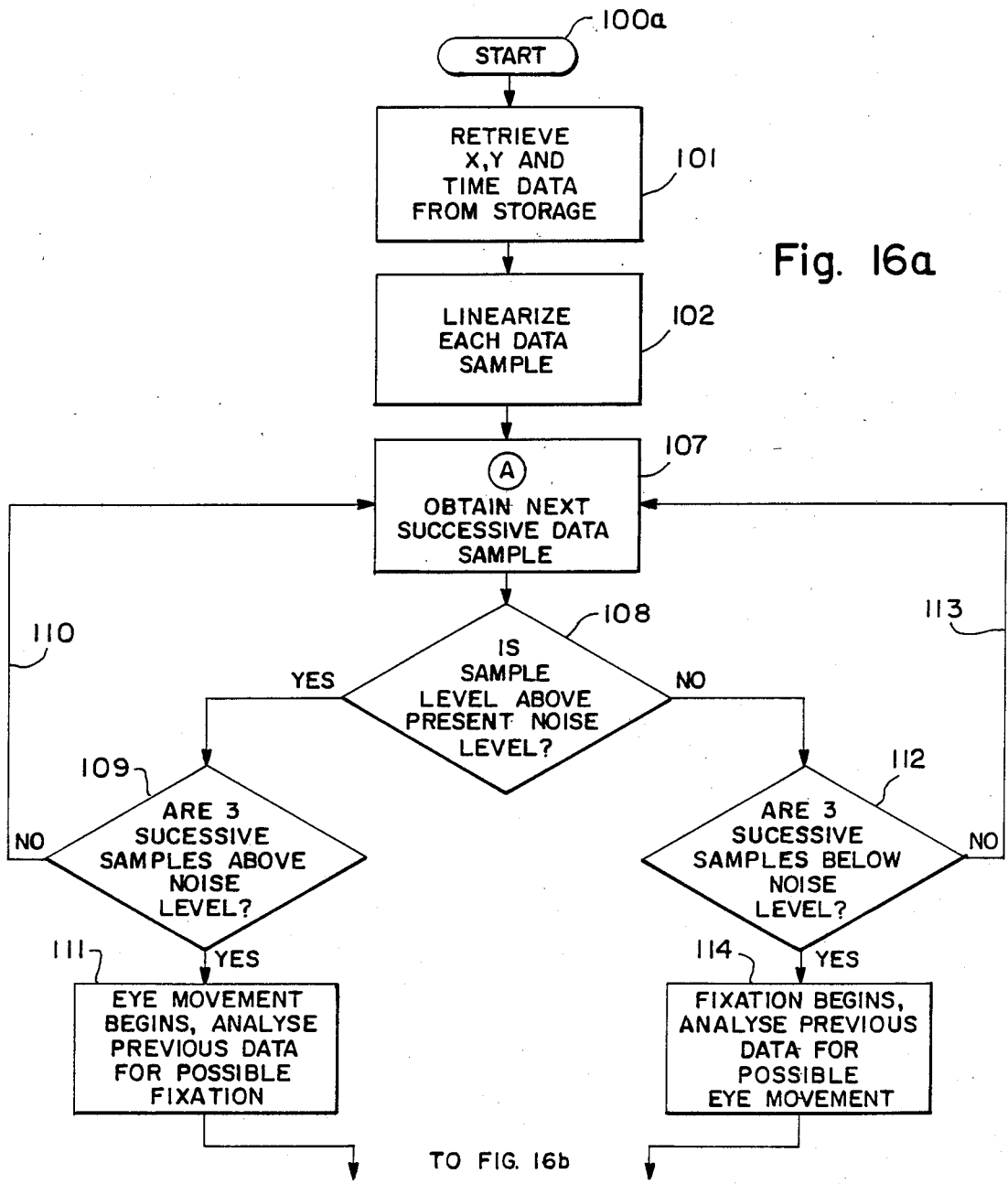
FIG. 16a is a system flow chart illustrating the first part of a data analysis program which obtains the collected data and distinguishes between fixations and eye movements.

At the time the program is initiated, at the start in FIG. 16a, at 100a, the x-y data, with the accompanying time data, is obtained from storage 16 in step 101 and linearized as indicated at step 102. The process of linearization begins before the subject is tested when a calibration sub-program is run which evaluates the signals received from a left fixation, a right fixation and a center fixation. The output of the eye movement detector is evaluated for each of these three fixations, the noise of each channel is calculated and stored, and these values are used for a mathematical algorithm that linearizes the numeric value of the data so that the same relative eye movement generates the same proportional signal on either side of center. If, for example, the subject does not have the 4 diodes equally positioned on each side of the iris, then the relative numerical value of the current flowing from the diodes will be distorted, since the respective triangulation between left and right fixations will not be equal. The calibration and linearization routine stores the numerical values received for the extreme left fixation, the center fixation, and the extreme right fixation together with the patient's name and test data. At the time the data are utilized, they are also linearized to compensate for triangulation or electronic component irregularities. The linearized data are then successively passed through the sub-routine, illustrated in FIG. 16a, which compares each successive x-y positional value to determine if an eye movement has occured. This program begins at step 107 wherein each successive sample is obtained following its categorization or classification.

The incoming data may consist of successive sets of x-y data at the beginning and end of each eye movement as previously described with respect to the data collection programs illustrated in FIGS. 14 and 15, respectively. In each of these programs, the linearized data consist of a set of x-y data at the beginning and end of each eye movement. Alternatively, a high speed processor may be used which will evaluate each successive data sample as indicated in FIG. 15 to isolate the transition points between fixations and eye movements, and to record time data accompanying the change in eye movement stats. The routine illustrated in FIG. 16a samples 3 successive positions before categorizing the data into any of the possible eye movements. These evaluations are to minimize the effect of random noise and temporary fluctuations in the electronic equipment. The analysis program, as indicated in FIG. 16a, consists of two primary branches of logic; one for fixations, and one for eye movements, with the eye movement loop being further subdivided into several sub-program loops. At the conclusion of each loop, the program is re-inserted at step 107 and return point A. Generally, all unknown data or data that does not fit the particular criteria are added to the fixation data. In addition, if the signals are within the noise level tolerance, they are stored as fixation data.

As indicated in FIG. 16a, the next successive sample is obtained, as indicated at step 107, and the sample is compared with the noise level limits as indicated at step 108. If the sample level is above noise level, it is then passed to the eye movement loop which begins with step 109. The next successive sample is obtained by return Loop 110. When three successive samples have been obtained above noise level, a program decision is made, at step 111, that an eye movement has begun, and there is a need to analyze the previous data for a possible fixation.

Alternately, if the sample, when compared at step 108, is below noise level, it is passed to the fixation loop which begins at step 112. If the sample difference as determined by step 112 is not above noise level, the sub-routine holds the sample and obtains the next successive sample via return loop 113. If three successive samples are below the noise level, then a program decision is made at step 114 that a fixation has begun, and there is a need to analyze the previous data for a possible eye movement. The previous data samples indicating a possible eye movement or a possible fixation are further processed in accordance with the program flow chart illustrated in FIG. 16b.

The program illustrated in FIG. 16a also constitutes, when used with a high speed processor, a data reduction program that will simplify the incoming eye movement data and establish the x-y coordinates and time values for the beginning of each eye movement and the beginning of each fixation. These values are then stored in temporary buffers as will be hereinafter discussed, or may be read to a temporary storage device for subsequent calculations and categorization.

Figure 16B:
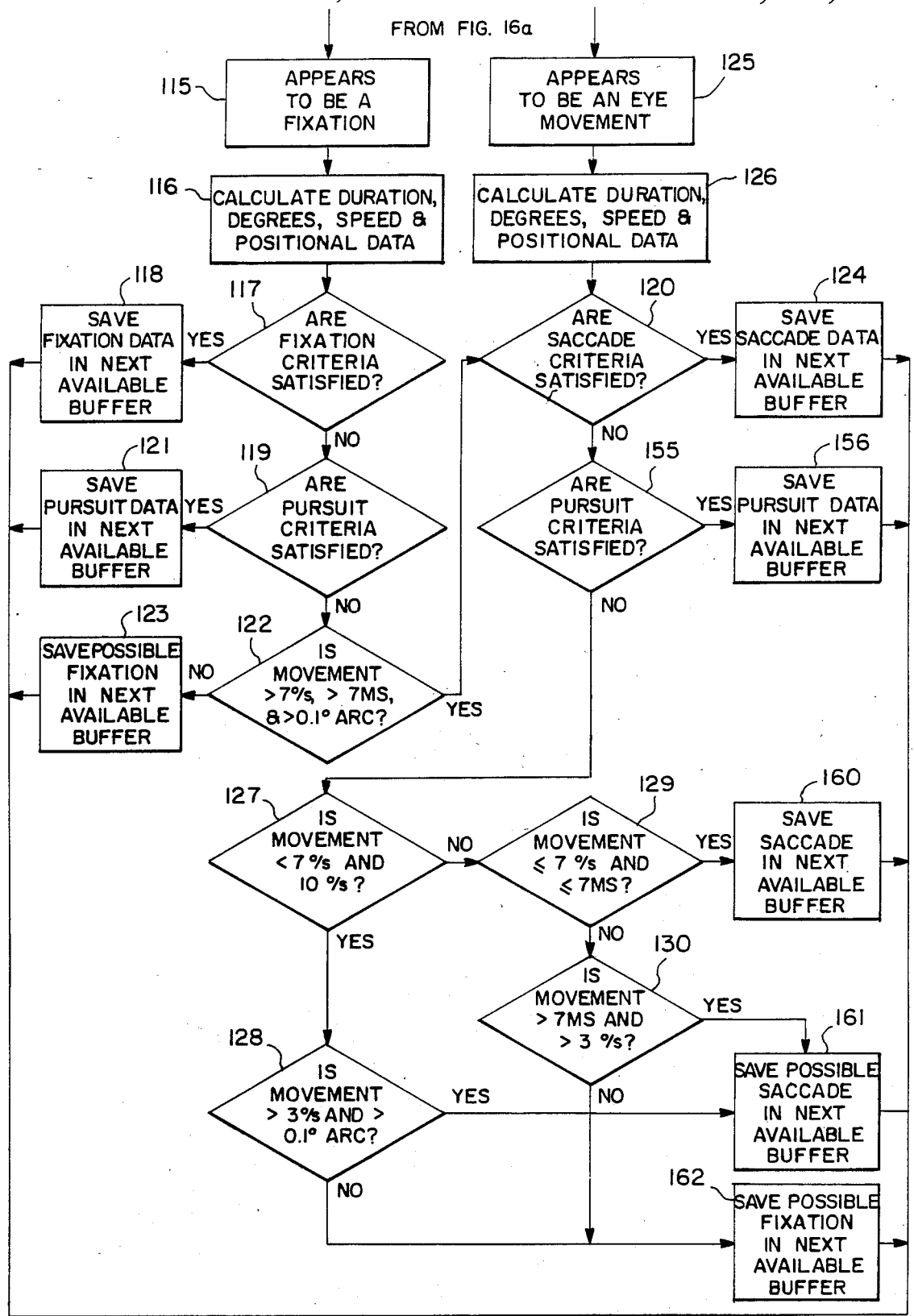
FIG. 16b is a system flow chart illustrating the second portion of a data analysis program which evaluates the collected data for fixations and eye movements.

The analysis evaluation begins with a sub-routine illustrated in FIG. 16b. If the data points isolated at step 111 appear to be a fixation, as determined by step 115, then calculations are made at step 116 with respect to the fixation, duration, relative eye movement, relative eye speed and positional data to determine if a fixation is possible. If the size of the eye movement is less than 0.1° of arc, the data are added to the fixation data. One major type of eye movement is termed micro-movement, which is used by the eye to continually shift image data on the retina. These micro-movements occur during fixation as part of the information gathering process. It is desirable, however, for the purpose of this program to treat micro-movements as part of the fixation. To qualify as a fixation, the size of the eye movement must be less than 0.1° of arc, and if the size of the eye movement is less than 0.1°, it is added to the fixation as possibly representing either noise or a micro-movement. In addition, if the speed of the eye movement is less than 0.5° per second, the eye movement is classified as a fixation. If all fixation criteria are satisfied at step 117, the fixation categorization is saved in the next available buffer as indicated at step 118. If, however, the fixation criteria are not satisfied at step 117, the program then performs calculations at step 119 to determine if the eye movement was a pursuit eye movement. To qualify as a pursuit eye movement, the eye movement must be greater than 0.1° of arc, the speed of the eye movement must be between 5° per second up to 7° per second, and the duration must be larger than 70 milliseconds. While pursuit can range from 0.5° per second up to 30° per second, for the purposes of this analysis program, maximum speed of any pursuit target is placed at 4° to 7° per second. Any higher speed must necessarily then be a saccade movement, and the data is then transferred to program step 120 after evaluation at step 22. If all pursuit criteria are satisfied at step 119, the pursuit eye movement is saved in the next available buffer as indicated at step 121. If these pursuit criteria are not satisfied, the data is then passed for further evaluation at step 122. If the speed is then greater than 7° per second, longer than 7 milliseconds, and covered more than 0.1° in arc, the eye movement data are passed through the decision point 120 wherein all saccade criteria have been satisfied and the saccade is saved in the next available buffer as indicated at step 124. If, however, the eye movement data does not fit the pursuit criteria or the saccade criteria of step 122, the data are saved as a possible fixation in the next available buffer as indicated at step 123. The program categorizes any unknown and undefinable eye movement as a fixation at step 123.

If the eye positional data isolated at step 114 in FIG. 16a indicates the beginning of a fixation, that eye positional data together with the previous data point are analyzed at step 125 for a possible eye movement. The x-y positional coordinates and the time data are then used at step 126 to calculate the duration, degree, speed and position of the eye movement.

If all of the saccade criteria are satisfied by this eye movement data at step 120, the saccade eye movement data is then stored in the next available buffer as indicated at step 124. The saccade eye movement is categorized or defined as an eye movement that is longer than 7 milliseconds, is greater than 0.1° in arc, with a speed of movement greater than 7° per second. If the eye movement calculated at step 126 does not fit within the saccade criteria, the movement data are then passed to decision step 155 to determine if the pursuit criteria are satisfied. As indicated previously, a pursuit movement is categorized as one greater than 0.1° in arc, greater than 70 milliseconds in duration, with a speed between 0.5° per second and 7° per second. If all pursuit criteria are satisfied at step 155, then the eye movement data are saved as a pursuit eye movement in the next available buffer as indicated at step 156. If a pursuit eye movement is not indicated, another evaluation is performed as indicated at step 127. If the duration has been less than 7 milliseconds, and the speed has been less than 10° of arc per second, then a final evaluation, is performed at step 128. If the duration or speed is greater than the criteria established at step 127, then a second level evaluation at step 129 is performed. This step 129 evaluates the movement to determine if the speed is equal to or less than 7° per second and if the duration is equal to and greater than 7 milliseconds. If this criteria are satisfied, the movement is then saved as a saccade in the next available buffer as indicated at step 160. If, however, the speed is not equal to or greater than 7° per second, or if the duration is not equal to or greater than 7 milliseconds, the a final evaluation step 130 is performed.

The evaluation criteria noted at steps 127–130 are used to classify marginal eye movements that do not fall squarely within the saccade and pursuit criteria previously defined by steps 120 and 155. If the duration is greater than 7 milliseconds, and the speed is greater than 3° per second, then the eye movement is saved by step 130 as a possible saccade in the next available buffer as indicated at step 161. Likewise, if step 128 determines that the speed is greater than 3° per second, and the size is greater than 0.1° of arc, the eye movement is stored as a possible saccade in the next available buffer at step 161. The remaining movements, which do not fit any of these previously defined criteria are saved as a possible fixation in the next available buffer as indicated at step 162. As indicated previously at step 123, any eye movement which does not fit certain predefined criteria is stored as a possible fixation.

Figure 16C:
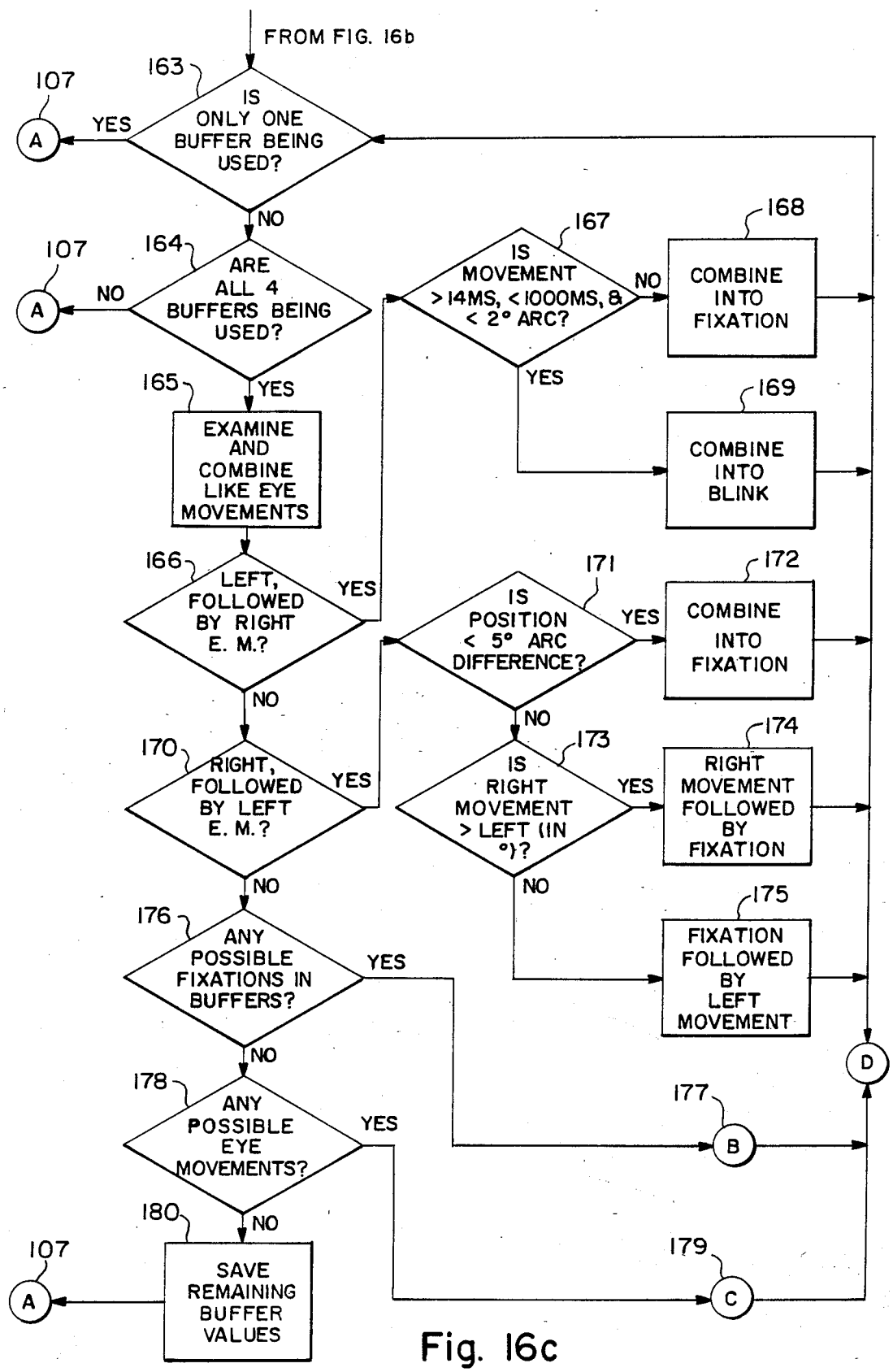
FIG. 16c is a system flow chart illustrating the third portion of a data analysis program which evaluates the categorized eye movements and fixations, and combines like movements when appropriate.

FIG. 16c illustrates a third portion of the analysis program which periodically checks the buffer capacity to combine like moves together and separate adjacent saccades in opposite directions into blinks rather than eye movements. At the end of the analysis indicated in FIG. 16b, the program checks at step 163 to see if only one buffer is being used. If only one buffer has been used, the program loop returns to point A in step 107 to compare the next successive sample described with respect to FIG. 16a. If there is more than one buffer being used, the program then examines the buffers to determine how many buffers are being used. When the program determines that all four buffers have been filled at step 164, the buffers are then examined in step 165 to combine the movements into like eye movements. If all four buffers are not being used, the program loop returns to point A in step 107 for the next successive sample.

After the four buffers have been filled, the first evaluation step 166 determines whether there are any left eye movements followed by an immediate right eye movement. This sub-routine removes blinks from the eye movement data. A blink will always appear as a left eye movement followed by a right eye movement by virtue of a manner in which the eyelid occludes the sclera during the blink. The distinction between the blink data and the saccade is two-fold. First, the duration is substantial, and secondly, the eye's physiology does not permit two successive saccade movements without a fixation therebetween. The evaluation at step 167 determines if the movement is in fact a blink. If, however, the total duration of the eye movement does not fit within the blink criteria, the movement is combined into the fixation data at step 168. To qualify as a blink, the eye movement must fall between 14 milliseconds and 1000 milliseconds, and the combined movements must transverse less than 2° of arc. If these criteria are met, the two eye movements are combined into a single blink at step 169.

The next evaluation at step 170 determines if there are any right eye movements followed by an immediate left eye movement. If so, the next evaluation at step 171 determines if the positional difference, in degrees, is less than 0.5° of arc. If it is, the combined movements are then stored as a single fixation at step 172. If not, another evaluation step 173 is performed to determine if the size of the right eye movement in degrees is greater than the size of the left eye movement in degrees. If so, the program at step 174 converts the data into a right eye movement followed by a fixation. If not, the data are combined at step 175 into a fixation followed by a left eye movement. Following the evaluations indicated at steps 166 and 170, the program at step 176 determines if any of the positional data in the buffers indicate a possible fixation If so, then another sub-routine at point B(illustrated in this figure as single step 177) will evaluate the fixation data using previous and following eye movements, as will be hereinafter discussed in more detail with respect to FIG. 16d.

Next, the program determines if any of the data stored in the buffer by steps 161 or 162 indicate possible eye movements. If movements are present, the program at step 178 determines if any possible eye movements are present, and if so, these possible eye movements are evaluated at point C in step 179 by using previous and following eye movements, as will be hereinafter described in further detail with respect to FIG. 16e. Following this evaluation at step 178, the program then saves all of the remaining buffer values to memory, as indicated at step 180, and returns to point A, in step 107, to process the next successive data sample.

Figure 16D:
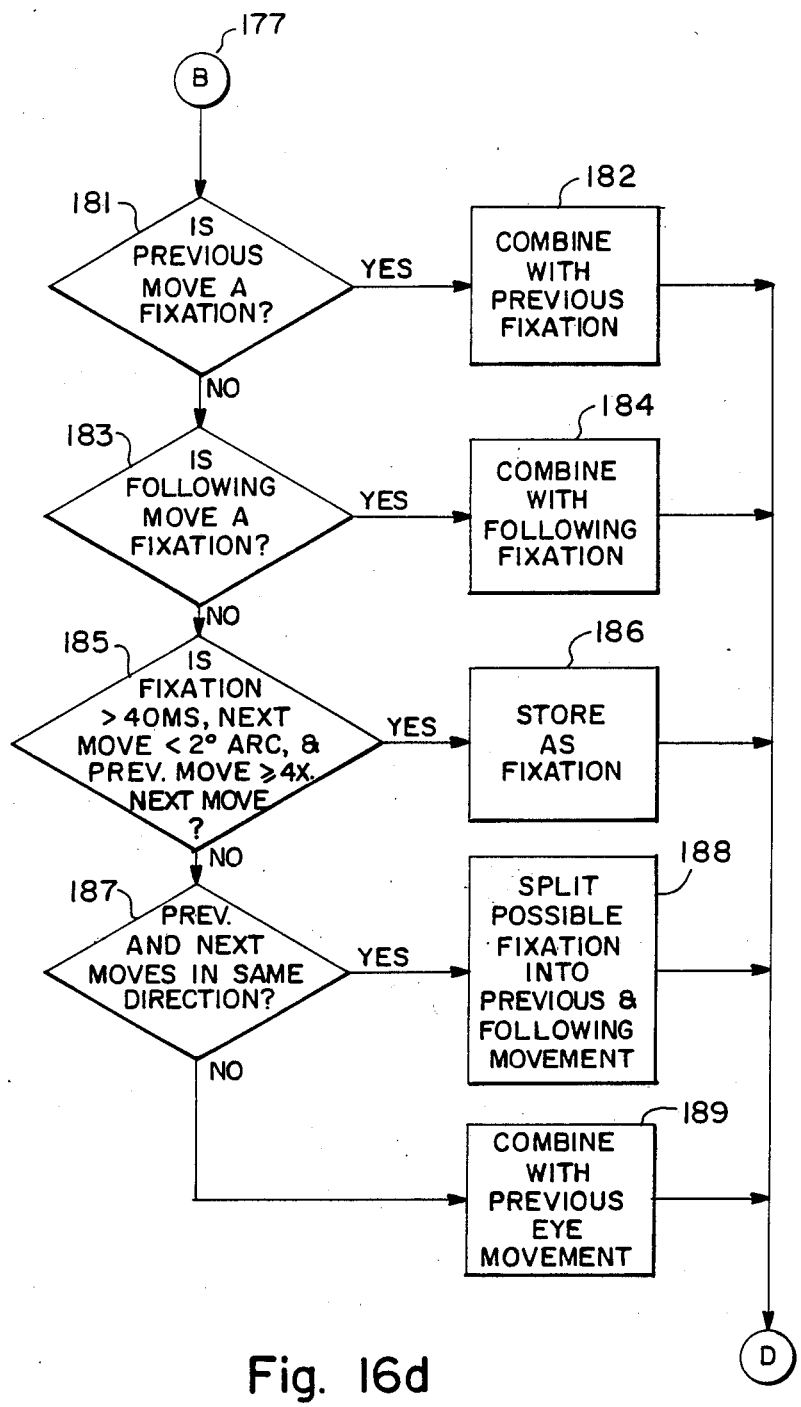
FIG. 16d is a system flow chart illustrating the fourth portion of a data analysis program which evaluates possible fixations for further classification.

FIG. 16d illustrates a sub-routine for the evaluation of possible fixations, and to make a determination as to whether a possible fixation should be categorized as a fixation or combined with a previous or following eye movement. At step 181, the first evaluation is to determine whether the immediately previous movement is also a fixation. If so, then this fixation is combined with the previous fixation at step 182. In the second evaluation, indicated at step 183, the program determines if the following eye movement is a fixation. If the following eye movement is a fixation, then the eye movement is combined at step 184 with the following fixation. The next evaluation at step 185 is a more comprehensive definition of a fixation that inquires to see if the duration of the fixation is greater than 40 milliseconds and whether or not the following eye movement is smaller than 2° of arc (with the size of the previous eye movement being equal to or greater than four times the size of the following eye movement). If so, this eye movement is categorized as a fixation and stored at step 186.

If the eye movement does not fit into these categories, then a final evaluation step 187, determines if the previous and following eye movements are in the same direction. If so, then the possible fixation is split between previous and following eye movements by step 188. If they are not in the same direction, the possible fixation is combined with the previous eye movement by step 189 and the sub-routine returns to the analysis program in FIG. 16c at point D.

Figure 16E:
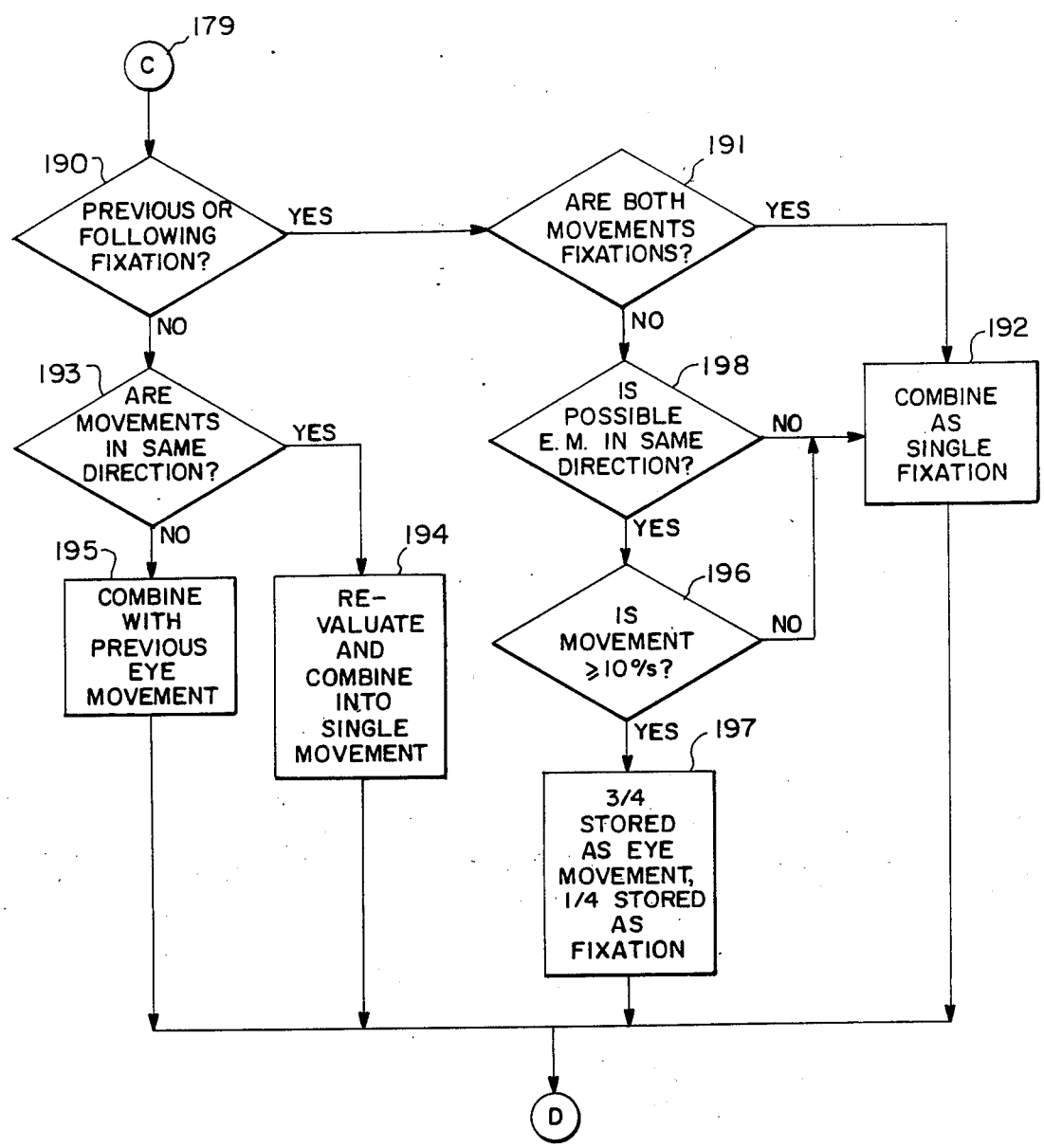
FIG. 16e is a system flow chart illustrating the fifth portion of a data analysis program which evaluates possible eye movements for further classification.

FIG. 16e discloses a separate sub-routine for the evaluation of a possible eye movement as previously noted at step 179. The first inquiry of the sub-routine at step 190 is to determine if there is a previous fixation or a following fixation. If either situation exists, a second determination, at step 191, determines if both the previous and the following movements are fixations. If so, the two fixations, and the intervening possible eye movement, are combined as a single fixation in step 192.

If there was no previous fixation or following fixation at step 190 the program determines if the previous and following eye movements are in the same direction at step 193. If both are in the same direction, the program then conducts a re-evaluation at step 194 to possibly combine all three eye movements as one. If not, the eye movement is combined with the previous eye movement, at step 195, and this combined eye movement is then stored in the next available buffer.

If the sub-routine has determined with steps 190 and 191 that only one of the previous and following eye movements is a fixation, a subsequent evaluation step 198 is conducted to determine if the possible eye movement is in the same direction as the immediately preceding or following eye movement. If not, the eye movement is combined at step 192 with either the preceding or following eye movements, and stored in the next available buffer. If the two movements were in the same direction, then a second evaluation step 196 determines if the speed of the movement is equal to or greater than 10° arc per second. If not, the movement is combined with a fixation at step 192. If it is equal to or greater than 10° arc per second, three-quarters of the possible eye movement is categorized with the eye movement, and one-fourth of the movement is categorized with the fixation by step 197 and the sub-routine returns to the analysis program at point D.

DETERMINATION OF DYSLEXIA

Figure 17:
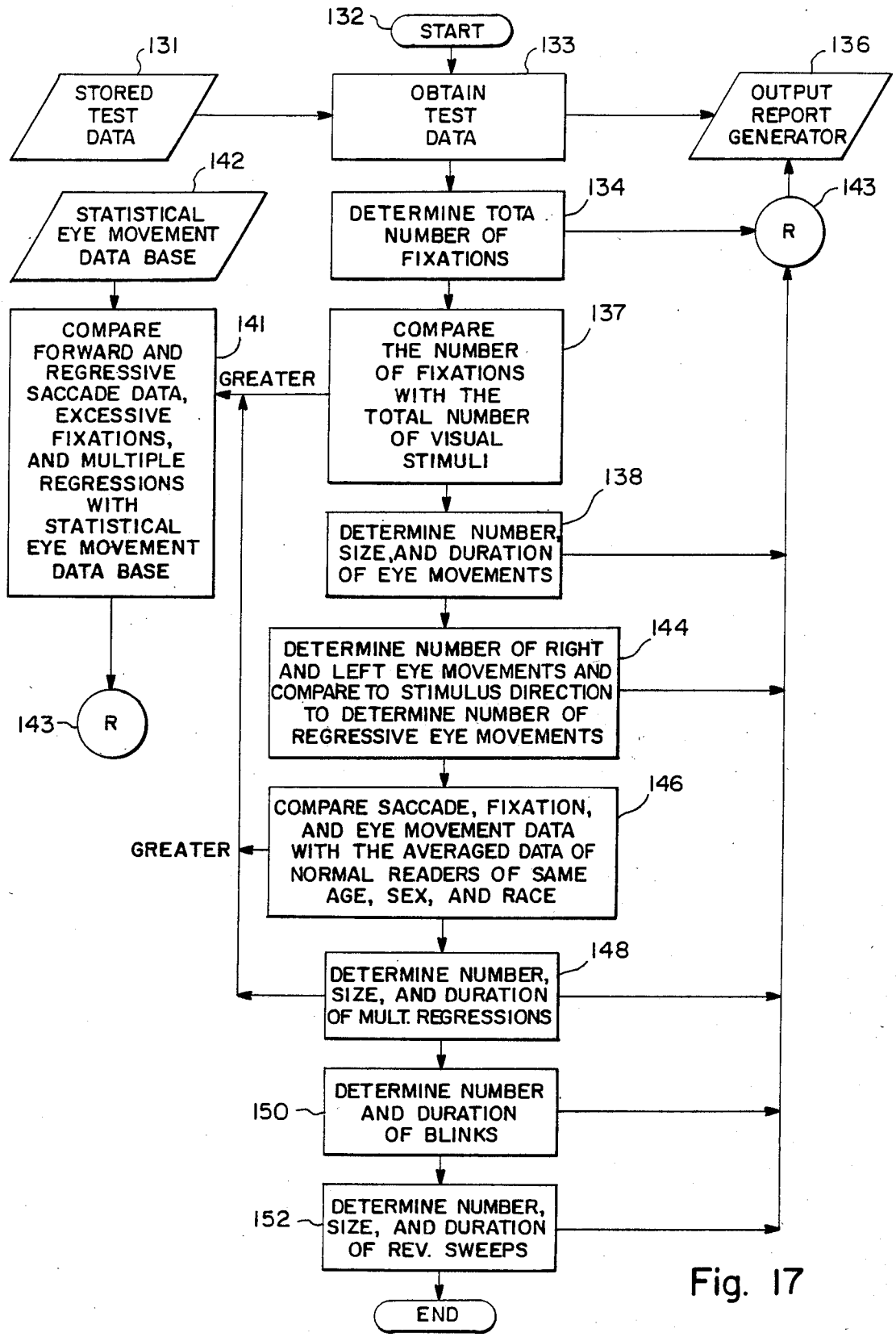
FIG. 17 is a system flow chart of a program for generating an output report on the test data analyzed in the program illustrated in FIG. 16a–16e, and comparing the test data, in the event of a dyslexia determination, with a statistical data base for determining the severity of the dyslexic condition, possible causes, and recommendations for treatment.

The final program, as illustrated in FIG. 17, compares certain parameters developed by the analysis program illustrated in FIGS. 16a–e and determines the existence and severity of dyslexia and other neurological conditions. After the program is initiated, at step 132, the stored test data 131 is obtained at step 133. This data has been stored in mass storage means 16, or on a removeable storage disk 19, or any other equivalent long-term storage device. The test results can then be sequentially printed out, as by output report generator 136, or an analysis may be performed on the test data. When an analysis is performed, the total number of fixations is determined, first, by step 134, and these are temporarily stored with the output report generator 136. The number of fixations is then compared with the total number of visual stimuli at step 137, and if the total number of fixations is greater than the number of visual stimuli, then the first indicator that dyslexia is present has been registered and the data are passed to the dyslexia comparator sub-routine 141. The analysis continues at step 138 as indicated.

The program contains a dyslexia comparator subroutine 141, which takes, at step 143 each of the objective parameters from the test data determined by steps 134, 138, 144, 148, 150 and 152 and compares the parameters with statistical data 142 that has been compiled over time. This data, at 142, categorizes empirical and historical eye movement data by age, sex, race and type of disorder. By continually updating the data base with the data from new test subjects, a data base is formed which defines the parameters associated with each type of disorder, and the incidence of occurance relative to the severity of the disorder.

Once the data from several hundred to a thousand subjects has been accumulated, the incoming eye movement parameters can be compared with existing historical parameters to diagnose the severity of the disorder. Based on the severity of the disorder and type of disorder, further recommendations can be stored in the data base as recommendation for further testing or apparent treatment. A graphic representation of the eye movement pattern, or a comparison of the subject's pattern with the historical data can also be sent to the output report generator 136 at step 143.

After the fixations have been determined and evaluated, then the total number, size and duration of eye movements is determined at step 138. The total number, size and durations of eye movements are then assembled with the rest of the report data in at step 143 and are sent to report generator 136. Following a determination of the total number of eye movements, the number of right and left eye movements are determined and compared with the direction of the stimulus channel to determine the number of regressive eye movements at step 144. The percentage and total amplitude of regressive eye movements are amongst the primary indicators of dyslexia, and this data is sent to output report generator 136, while the analysis continues at step 146 as indicated.

As noted previously in Table 1, the percentage of regressive saccades for retarded readers, normal readers and advanced readers stabilized between 6.8% and 9.8%, while the percentage of regressive saccades manifested by dyslexics averaged 29.9%. If the percentage, total number, size, duration of forward and regressive saccades and the fixations and eye movements that precede and follow them is higher than the average for the normal readers of the same age, sex, and race, then the data is passed to the dyslexia comparator sub-routine 141 by program step 146. The analysis continues at step 148. In addition to the number of fixations and regressive saccades, the total number, size and duration of multiple regressions also indicates dyslexia. This number is calculated as indicated at step 148, and the total number is passed to both the report generator at step 143, and the dyslexia sub-routine 141. The analysis continues at step 150–152 as indicated.

The total number and duration of blinks are also calculated at step 150, and passed to the output report generator at step 143. In a normal test, the number of blinks will be minimal. However, if the light test is too difficult for the subject, the number of blinks may increase. Also, hyperactive attentionally handicapped children may also show an increased number of blinks. Finally, the total number, size and duration of reverse sweeps is also tabulated at step 152 inasmuch as a number of reverse sweeps may also indicate dyslexia. This data is also passed to the output generator at step 143 as shown. A reverse sweep indicates the subject is having difficulty with landing the eye on target. Reverse sweeps are frequent in reading tests where subjects go back from the end of one line to the beginning of the next. However, when the stimulus is a series of flashing lights, the number of reverse sweeps may indicate inability to accurately direct the eyes to the stimulus.

The dyslexia comparator sub-routine 141 compares the percentage, total number, size and duration of forward and regressive saccades, excessive fixations, and multiple regressions with statistical data previously assembled by testing dyslexics, retarded readers, normal readers and other subjects. The percentage of regressions and the number of fixations is then interpolated along a scale using standard deviation or least square regression and other statistical techniques to determine the severity of the dyslexia in comparison with other known dyslexic subjects of the same age, sex and race. The output of the comparative report is then passed to the output report generator at step 143.

Finally, an output report is printed from the output report generator program 136 as indicated in FIG. 1. The output report may take several forms depending upon the desire of the operator Depending upon the system selected and the desire of the operator, the report may be rendered in alphanumeric and graphic form on a video display, may be stored on a storage disk, may be printed out on a plotter, a strip chart recorder 20 or may be printed and tabulated at printer 21.

Alternately, the invention may be practiced, as illustrated in FIG. 1, with a combination of graphics and an output diagnosis indication as to whether or not the subject has dyslexia, or other neurological conditions, and if so, the relative severity of the dyslexia or of the condition under test. After the dyslexia diagnosis is made, recommendations are made about the possible cause of the problem and for further testing and/or appropriate methods of treatment. The percentile placement of the subject in relation to the general population may also be given graphically. Additionally, a graphic representation of the eye movement location in relation to the stimulus position may be given. The order of occurrence, duration, size, location and speed of each of the eye movements, blinks and fixations may be printed alongside the beginning point of each of them. Statistical bar graphics representing the results of the diagnosis may also be printed. The combination of the easy to read graphics and the verbal diagnosis and recommendations for further testing, the possible causes of the condition, and suggestion for appropriate methods of treatment makes the test device both complete and easily comprehensible.

I claim:

1. An automated system for determining the existence of dyslexia, said system comprising:
    (a) means for stimulating a predetermined pattern of eye movement in a subject to be tested for dyslexia,
    (b) means for detecting eye movement in a subject observing said means for stimulating eye movement, said detecting means providing an electrical output signal in response to said movement,
    (c) processor means for receiving said electrical output signal, said processor means further including,
        (i) means for sampling the output signal to obtain a series of successive eye positions,
        (ii) means for converting said successive eye positions into data representing eye movements,
        (iii) means for analyzing said data by direction, duration and amplitude in order to differentiate between forward saccadic movements, reverse saccadic movements, pursuit movements and fixations,
        (iv) means for comparing the number and placement of reverse saccadic eye movements with predetermined patterns to determine the existence of dyslexia,
    (d) output means for enabling display of said diagnosis.

2. An automated system for determining the existence of dyslexia, said system comprising:
    (a) means for stimulating a predetermined pattern of eye movement in a subject to be tested for dyslexia,
    (b) means for detecting eye movement in a subject observing said means for stimulating eye movement, said detecting means providing an electrical output signal in response to said movement,
    (c) processor means for receiving said electrical output signal, said processor means further including,
        (i) means for sampling the output signal to obtain a series of successive eye positions,
        (ii) means for linearizing and converting said successive eye positions into data representing eye movements, said linearization being conducted on the successive eye positions,
        (iii) means for analyzing said eye movements and differentiating between forward and reverse saccadic movements, pursuit movements and fixations,
        (iv) means for comparing said eye movements to predetermined patterns determine the existence of dyslexia,
    (d) output means for enabling display of said diagnosis.

3. An automated system for determining the existence of dyslexia, said system comprising:
    (a) means for stimulating a predetermined pattern of eye movement in a subject to be tested for dyslexia,
    (b) means for detecting eye movement in a subject observing said means for stimulating eye movement, said detecting means providing an electrical output signal in response to said movement,
    (c) processor means for receiving said electrical output signal, said processor means further including,
        (i) means for sampling the output signal to obtain a series of successive eye positions,
        (ii) means for converting said successive eye positions into data representing eye movements,
        (iii) means for analyzing said eye movements and differentiating between forward and reverse saccadic movements, pursuit movements and fixations,
        (iv) means for comparing the accuracy of the eye position over time with respect to the stimulus to diagnose dyslexia,
    (d) output means for enabling display of said diagnosis.

4. An automated system for determining the existence of dyslexia as claimed in claim 1 or 2 or 3, said system further comprising a calibration means for linearizing the output signals from said eye movement detector means, before said signals are differentiated into eye movements.

5. An automated system for determining the existence of dyslexia as claimed in claim 1 or 2 or 3, wherein said means for stimulating eye movement includes a series of sequentially, illuminated stimuli, arranged in a lateral array.

6. An automated system for determining the existence of dyslexia as claimed in claim 4, wherein said means for stimulating eye movement include a series of photo diodes mounted on the eye movement detector to be viewed by the subject through a partially reflective mirror.

7. An automated system for determining the existence of dyslexia as claimed in claim 5 wherein said diodes are spaced to provide approximately 2°–6° of eye movement between each diode.

8. An automated system for determining the existence of dyslexia as claimed in claim 1 or 2 or 3, wherein said means for stimulating eye movements includes a synchronization means for correlating detected eye movements with a predetermined stimuli.

9. An automated system for determining the existence of dyslexia as claimed in claim 7, wherein said predetermined stimuli appear on an electronic display device.

10. An automated system for determining the existence of dyslexia as claimed in claim 7, wherein said stimuli include a slowly moving stimulus to stimulate pursuit eye movement in the observer.

11. An automated system for determining the existence of dyslexia as claimed in claim 7, wherein said stimulus includes a plurality of stimuli that may be synchronously activated, randomly activated or sequentially activated in a lateral direction.

12. An automated system for determining the existence of dyslexia as claimed in claim 1 or 2 or 3, wherein said means for converting said successive eye positions into data converts said positions into x-y coordinate values.

13. An automated system for determining the existence of dyslexia as claimed in claim 1 or 2, wherein said means for analyzing said data compares the length and location of a fixation period with the length and location of a fixation stimulus.

14. An automated system for determining the existence, severity and kind of dyslexia as claimed in claim 1 2 or 3, wherein said means for analyzing said data and categorizing said eye movement compares the average and total length of forward and regressive eye movements with the average and total length of all eye movements combined.

15. An automated system for determining the existence of dyslexia as claimed in claim 1 or 2 or 3, wherein said output means also displays eye movement categories as a series of x-y movements in relation to time.

16. An automated system for determining the existence of dyslexia as claimed in claim 2 or 3, wherein the existence of dyslexia is determined by comparing the percentage of saccadic regressions with a predefined statistical average.

17. An automated system for determining the existence of dyslexia as claimed in claim 2 or 3, determined statistical parameters to determine the severity of dyslexia.

18. An automated system for determining the existence of dyslexia as claimed in claim 1 or 2 or 3, wherein said means for detecting eye movements includes a diode array.

19. An automated system for detecting the existence of dyslexia as claimed in claim 18, wherein said diode array is a linear array.

20. A method for identifying the existence of dyslexia, said method comprising:
    (a) stimulating eye movement in a subject to be tested for dyslexia,
    (b) detecting eye movement in said subject being stimulated, and converting the magnitude and direction of eye movement to an electronic signal,
    (c) sampling the electronic signal at intervals and converting said samples to data representing eye positions,
    (d) automatically analyzing said data samples by direction, duration and amplitude with an electronic data processor and according to a predetermined program to differentiate saccadic movements, pursuit movements and fixations,
    (e) comparing the number and placement of regressive saccade movements with predetermined patterns of movements to determine the existence of dyslexia.

21. A method for identifying the existence of dyslexia as claimed in claim 20 which further comprises the step of linearizing the output signals from said eye movement detector before said signals from said eye movement detector are analyzed.

22. A method for identifying the existence of dyslexia as claimed in claim 20 or 21 which further includes stimulating eye movement in the observer with sequentially illuminated stimuli arranged in a lateral array.

23. A method for identifying the existence of dyslexia as claimed in claim 20 or 21, which further comprises the step of synchronizing the detected eye movements with a predetermined stimulus.

24. A method for identifying the existence of dyslexia as claimed in claim 20 or 21, wherein the step of stimulating eye movement is performed with one or more stimuli created on the face of an electronic display device.

25. The new use of a computer in diagnosing dyslexia, said use comprising:
    (a) generating a signal to initiate a visual stimulus for observation by an individual to be diagnosed,
    (b) sampling an electrical signal created by an eye movement detector to distinguish between saccadic movements and pursuit eye movements,
    (c) recording only those samples which indicate a change in eye movement,
    (d) analyzing said recorded samples to determine at least the direction, duration and amplitude of the movements in order to differentiate between forward and reverse saccade movements, pursuit movements and fixations,
    (e) comparing the patterns of eye movements with a predefined pattern to determine if dyslexia is present.

26. The new use of a computer in diagnosing dyslexia as claimed in claim 25, wherein the visual stimuli are generated on a cathode ray tube.

27. The new use of a computer as claimed in claim 26 which further includes the step of initiating a series of sequentially illuminated stimuli, where said stimuli are arranged in a lateral array.

28. The new use of a computer as claimed in claim 25 or 26 wherein the percentage of regressive saccade movements is compared with a predetermined percentage to determine dyslexia.

* * * * *

UNITED STATES PATENT AND TRADEMARK OFFICE
CERTIFICATE OF CORRECTION

PATENT NO. : 4,889,422

DATED : December 26, 1989

INVENTOR(S) : George Pavlidis

It is certified that error appears in the above-identified patent and that said Letters Patent is hereby corrected as shown below:

Column 1, line 64: after "intelligence." insert new paragraph to read --PRIOR ART STATEMENT--

Column 2, line 1: "disclosed testing" should read as --disclosed a testing--

Column 2, line 64: "electro oculographic" should read as --electro-oculographic--

Column 2, line 65: "stimuli This" should read as --stimuli. This--

Column 6, line 15: "saccade This" should read as --saccade. This--

Column 6, line 21: "duration The" should read as --duration. The--

Column 6, line 24: "after line" should read as --after line.--

Column 10, line 49: "operator The" should read as --operator. The--

UNITED STATES PATENT AND TRADEMARK OFFICE
CERTIFICATE OF CORRECTION

PATENT NO. : 4,889,422

DATED : December 26, 1989

INVENTOR(S) : George Pavlidis

It is certified that error appears in the above-identified patent and that said Letters Patent is hereby corrected as shown below:

Column 16, line 66: "stats" should read as --status--

Column 18, line 6: "5°" should read as --0.5°--

Column 22, line 1: delete "in"

Column 22, lines 64 and 65: "operator Depending" should read as --operator. Depending--

Column 23, line 26: "I claim:" should read as --In The Claims:--

Column 26, line 45, Claim 27: "claim 26" should read as --claim 25 or 26--

Signed and Sealed this

Thirteenth Day of August, 1991

Attest:

HARRY F. MANBECK, JR.

*Attesting Officer*      *Commissioner of Patents and Trademarks*